US009906190B2

(12) United States Patent
Jones

(10) Patent No.: US 9,906,190 B2
(45) Date of Patent: Feb. 27, 2018

(54) SOIL MONITORING SYSTEM

(71) Applicant: Ryan Bower Jones, Carlsbad, CA (US)

(72) Inventor: Ryan Bower Jones, Carlsbad, CA (US)

( * ) Notice: Subject to any disclaimer, the term of this patent is extended or adjusted under 35 U.S.C. 154(b) by 0 days.

(21) Appl. No.: 15/173,821

(22) Filed: Jun. 6, 2016

(65) Prior Publication Data
US 2016/0359453 A1 Dec. 8, 2016

Related U.S. Application Data

(60) Provisional application No. 62/171,187, filed on Jun. 4, 2015, provisional application No. 62/216,257, filed on Sep. 9, 2015, provisional application No. 62/273,267, filed on Dec. 30, 2015, provisional application No. 62/254,401, filed on Nov. 12, 2015.

(51) Int. Cl.
*G01R 31/26* (2014.01)
*H02S 50/00* (2014.01)
*G01N 21/94* (2006.01)
*G01R 31/40* (2014.01)

(52) U.S. Cl.
CPC ............. *H02S 50/00* (2013.01); *G01N 21/94* (2013.01); *G01R 31/40* (2013.01)

(58) Field of Classification Search
CPC ........ G01R 31/08; G01R 31/26; G01R 31/40; H02S 40/00; H02S 40/10; H02S 40/32; H02S 40/36; H02S 50/00; H02S 50/10; H02J 3/16; H02J 3/283; H02J 3/285; H02J 3/286; G05F 1/67
See application file for complete search history.

(56) References Cited

U.S. PATENT DOCUMENTS 8,725,437 B2 * 5/2014 Caine ..................... H02S 50/10
702/58
9,154,075 B2 * 10/2015 Chen ..................... G01K 13/00
(Continued)

FOREIGN PATENT DOCUMENTS

| WO | 2010135321 | 2/2011 |
|----|------------|--------|
| WO | 2014081967 | 5/2014 |

OTHER PUBLICATIONS

International Search Report and Written Opinion of the International Searching Authority dated Sep. 8, 2016, for International Application No. PCT/US16/35966.

*Primary Examiner* — Minh N Tang
(74) *Attorney, Agent, or Firm* — Matthew M. Googe; Robinson IP Law, PLLC

(57) ABSTRACT

A solar panel soiling monitoring system is provided for measuring soiling losses on a photo-voltaic system. The solar panel monitoring system includes: a soil monitoring panel including a plurality of arranged photovoltaic cells connected in series to one another; a measurement unit in electronic communication with a switchbox for controlling measurements of each of the photovoltaic cells; a communication unit in electronic communication with the measurement unit; and a data storage system in electronic communication with the communication unit including a processor, a computer readable storage medium, and one or more computer programs operable on the data storage system. The data storage system determines soiling conditions of the soil monitoring panel based on measured short circuit currents of each of the plurality of photovoltaic cells of the soil monitoring panels.

20 Claims, 23 Drawing Sheets

(56) References Cited

U.S. PATENT DOCUMENTS

| | | | |
|---|---|---|---|
| 2012/0053867 A1* | 3/2012 | Dunn | H02S 50/10 702/58 |
| 2014/0077608 A1 | 3/2014 | Nosaka et al. | |
| 2014/0100698 A1 | 4/2014 | Suresh et al. | |

\* cited by examiner

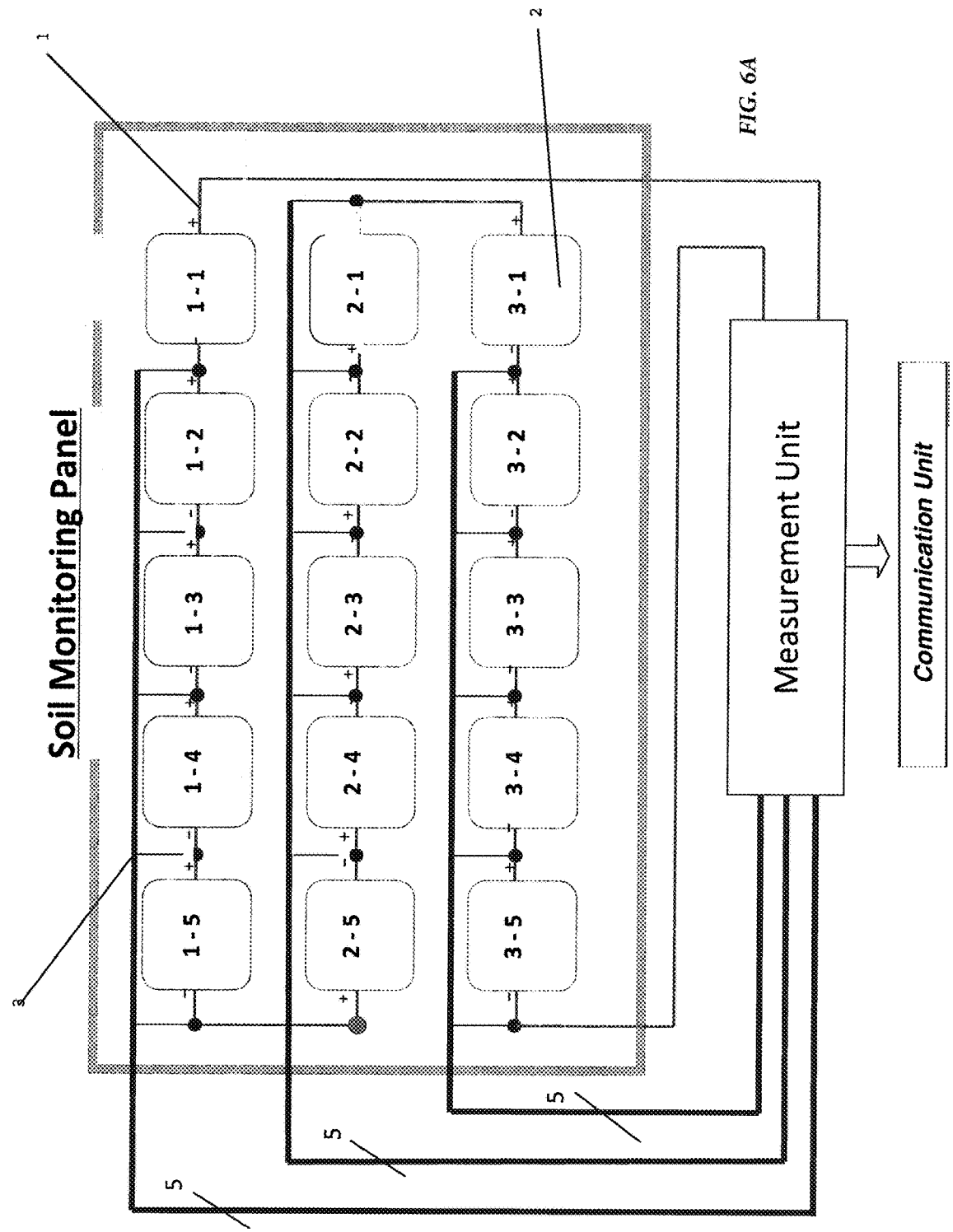

SOIL MONITORING SYSTEM

CROSS-REFERENCES TO RELATED APPLICATIONS

This application claims priority to U.S. Patent Application Ser. No. 62/171,187 by Ryan B. Jones for a "Soil Panel Monitoring System", which was filed on Jun. 4, 2015, U.S. Patent Application Ser. No. 62/216,257 by Ryan B. Jones for a "PV Soil Monitoring Platform", which was filed on Sep. 24, 2015, U.S. Patent Application Ser. No. 62/273,267 by Ryan B. Jones for a "Soil Monitoring System for Photovoltaic Panels", which was filed on Dec. 30, 2015, and U.S. Patent Application Ser. No. 62/254,401 by Ryan B. Jones for "An Automated System for Cleaning a PV Reference Panel, Single Piece of Glass, or Other Suitable Surface", which was filed on Nov. 12, 2015, the contents of which are incorporated by reference herein in their entireties.

FIELD

This disclosure relates to the field of photovoltaic panels. More particularly, this disclosure relates to a solar panel soiling monitoring system for monitoring reduced power generated by solar panels as they become contaminated by dust and dirt that may obscure a face of the panels during use.

BACKGROUND

Solar panels utilize the energy from the sun and convert this into electrical energy. In order to maximize the energy production of the solar panels, they must remain clean. Cleaning panels on large-scale PV plants or rooftop commercial PV plants can be expensive, and it is important to understand the required frequency and timing of the cleanings in order to optimize the performance of the PV plant and minimize costs.

Thus, a solar panel soiling monitoring system solving the aforementioned problems is desired.

SUMMARY

The above and other needs are met by a solar panel monitoring system for measuring soiling losses in a photo-voltaic system. In a first aspect, a solar panel soiling monitoring system for a photo-voltaic (PV) system is provided, the monitoring system including: a soil monitoring panel including a plurality of arranged photovoltaic cells arranged on a rectangular frame and connected in series to one another; a measurement unit including a circuit board in electronic communication with a switchbox for controlling measurements of each of the plurality of photovoltaic cells of the soil monitoring panel, the measurement unit in electronic communication with each of the plurality of photovoltaic cells of the solar monitoring panel; a communication unit in electronic communication with the measurement unit and including a device for transmitting a detected short circuit current of each individual photovoltaic cell of the plurality of photovoltaic cells; and a data storage system in electronic communication with the communication unit including a processor, a computer readable storage medium, and one or more computer programs operable on the data storage system. The data storage system determines soiling conditions of the soil monitoring panel based on measured short circuit currents of each of the plurality of photovoltaic cells of the soil monitoring panels.

In one embodiment, the solar panel monitoring system includes a reference solar panel including at least one photovoltaic cell in electronic communication with the data acquisition system, wherein the data acquisition system receives a short circuit current of the at least one photovoltaic cell of the reference solar panel and wherein the data storage system further determines conditions of the soil monitoring panel based on compared measured short circuit currents of each of the plurality of photovoltaic cells of the soil monitoring panel and the at least one photovoltaic cell of the reference solar panel. In another embodiment, the reference solar panel is positioned at a same azimuth and elevation angle as the soil monitoring panel.

In yet another embodiment, the reference solar panel further comprises an automatic cleaning system, the cleaning system including one or more movable cleaning components mounted adjacent to the reference solar panel, the one or more movable cleaning components including one or more motors in communication with a controller, wherein the controller activates the one or more movable cleaning components for cleaning a surface of the reference solar panel.

In one embodiment, one of the one or more movable cleaning components comprises a dry brush for sweeping a surface of the reference solar panel.

In another embodiment, the soil panel monitoring system further includes a fluid tank and a spray manifold adjacent the reference panel in fluid communication with the fluid tank, wherein one of the one or more movable cleaning components comprises a squeegee. In yet another embodiment, the spray manifold is mounted to an arm attaching the squeegee to the motor. In one embodiment, the solar panel monitoring system further includes a housing positioned adjacent the reference solar panel for housing the one or more movable cleaning components when not in use.

In one embodiment, the solar panel monitoring system further includes one or more environmental condition sensors in electronic communication with tone of the data storage system, communications unit, or measurement unit, the one or more environmental condition sensors selected from the group consisting of a temperature sensor, rain or moisture sensor, and a wind sensor.

In another embodiment, the soil monitoring panel has a size and dimensions that are proportional to one or more solar panels of an adjacent photovoltaic system.

In yet another embodiment, the solar panel monitoring system further includes a communications module in electronic communication with the data acquisition system for communicating with a remote server database.

In one embodiment, the solar panel monitoring system further includes a communications module in electronic communication with the measurement unit, wherein the data acquisition system is located remotely from the soil monitoring solar panel and receives data remotely via the communications module.

In another embodiment, the solar panel monitoring system includes a bypass switch in electronic communication with the plurality of photovoltaic panels connected in series and in communication with the data storage system, wherein when the bypass switch is activated the plurality of series connected photovoltaic panels are disconnected from a power supply for measuring a short circuit current of the photovoltaic panels.

In yet another embodiment, the solar panel monitoring system includes a forecasting module implemented on the data storage system, wherein the forecasting module determines a cleaning schedule of a photovoltaic system based on a determined soiling rate of the soil monitoring panel.

In one embodiment, the solar panel monitoring system further includes a Bypass Unit, consisting of one or more load break disconnect switches which are controlled by a logic circuit in order to connect and disconnect a plurality of series connected pv panels from the load and connecting or disconnecting the plurality of series connected pv panels from one or more Soil Monitoring panels (may be the Soil Monitoring panel of claim 1 or any standard PV panel). In another embodiment, the bypass unit includes switching devices in communication with a logic, control and or communications unit, whereby controlling the connection or disconnection of one or more Soil Monitoring panels to a Measurement Unit. In yet another embodiment, the solar panel monitoring system includes a bypass switch in electronic communication with the plurality of photovoltaic panels connected in series and in communication with a Communications Unit, wherein when the bypass switch is activated the plurality of series connected photovoltaic panels are disconnected from a power supply and from the panel(s) to be measured for soiling loss, and reconnected to the power supply albeit without connection to the panel(s) to be measured for soiling loss. When the soil measurements have been taken the Communications Unit signals for the Bypass Switch to disconnect the plurality of series connected PV panels from the power supply once again, and reconnect the soil Monitoring panel(s) to the plurality of series connected pv panels and to the power supply.

In a second aspect, a method of determining a soiling condition of a photo-voltaic system is provided, the method including: (1) providing a soil monitoring panel having a plurality of arranged photovoltaic cells; (2) providing a measurement unit in electronic communication with each of the individual photovoltaic cells of the soil monitoring panel; (3) providing a data acquisition system including a processor, a computer readable storage medium, and one or more computer programs operable on the data acquisition system; (4) providing a communications unit for communicating with a server database; (5) measuring a short circuit current of each of the individual photovoltaic cells via the switchbox on the measurement unit; (6) comparing measured short circuit currents of each of the individual photovoltaic cells with other of the individual photovoltaic cells of the soil monitoring panel; (7) determining soiling conditions of the soil monitoring panel based on measured and compared short circuit currents of the individual photovoltaic cells.

In one embodiment, the method of determining a soiling condition of a photo-voltaic system further includes: providing a reference solar panel including at least one reference photovoltaic cell; measuring a short circuit current of the at least one reference photovoltaic cell on the data storage system; measuring a maximum power point of at least one reference photovoltaic cell connected to the measurement unit; comparing measured short circuit currents of each of the individual photovoltaic cells with the measured short circuit current of the reference photovoltaic cell; determining soiling conditions of the soil monitoring panel based on measured and compared short circuit currents of the individual photovoltaic cells and the reference photovoltaic cell.

In a third aspect, a solar panel monitoring system is provided including: a soil monitoring panel including a plurality of arranged photovoltaic cells; a measurement unit including a circuit board in electronic communication with each of the plurality of photovoltaic cells of the soil monitoring panel; a communications unit for receiving a short circuit current from each individual photovoltaic cell of the plurality of photovoltaic cells via the junction box; and a data acquisition system including a processor, a computer readable storage medium, and one or more computer programs operable on the data acquisition system; a reference solar panel including at least one photovoltaic cell in electronic communication with the data acquisition system, wherein the data acquisition system receives a short circuit current of the at least one photovoltaic cell of the reference solar panel and wherein the data acquisition system further determines conditions of the soil monitoring panel based on compared measured short circuit currents of each of the plurality of photovoltaic cells of the soil monitoring panel and the at least one photovoltaic cell of the reference solar panel. The data acquisition system receives a short circuit current of the at least one photovoltaic cell of the reference solar panel and a short circuit current of each of the plurality of arranged photovoltaic cells of the soil monitoring panel. The data acquisition system determines conditions of the soil monitoring panel based on compared measured short circuit currents of each of the plurality of photovoltaic cells of the soil monitoring panel and the at least one photovoltaic cell of the reference solar panel.

BRIEF DESCRIPTION OF THE DRAWINGS

Further features, aspects, and advantages of the present disclosure will become better understood by reference to the following detailed description, appended claims, and accompanying figures, wherein elements are not to scale so as to more clearly show the details, wherein like reference numbers indicate like elements throughout the several views, and wherein:

1. Soil Monitoring Panel Connectors
  2. Measurement Unit Connectors
  3. Electronic Enclosure J-box
  4. Electronic Enclosure J-box
  5. Connector Capture Plate
  6. Panel J-box (back side view)
  7. Connector Platform
  8. Hole where Flex PCB enters
  9. Screw mounts from Connector Capture Plate
  10. Screw mounts to mount to Panel J-box
  11. Connector hole—top of Panel connector protrudes
  12. Connector Capture Plate—bottom of the connector is captured while top of the connector protrudes

FIG. 6A shows a block diagram showing the connection to the PV cells to the Measurement Unit in a Soil Monitoring panel and Reference Panel. This example shows 30 cells but any number of cells can be connected;
1. Series connection wire connecting all cells in series for MPPT and Charging
2. PV Cells
3. Additional −/+ connections for each cell in order to measure Isc of each cell on the PV panel

Figure 8A:
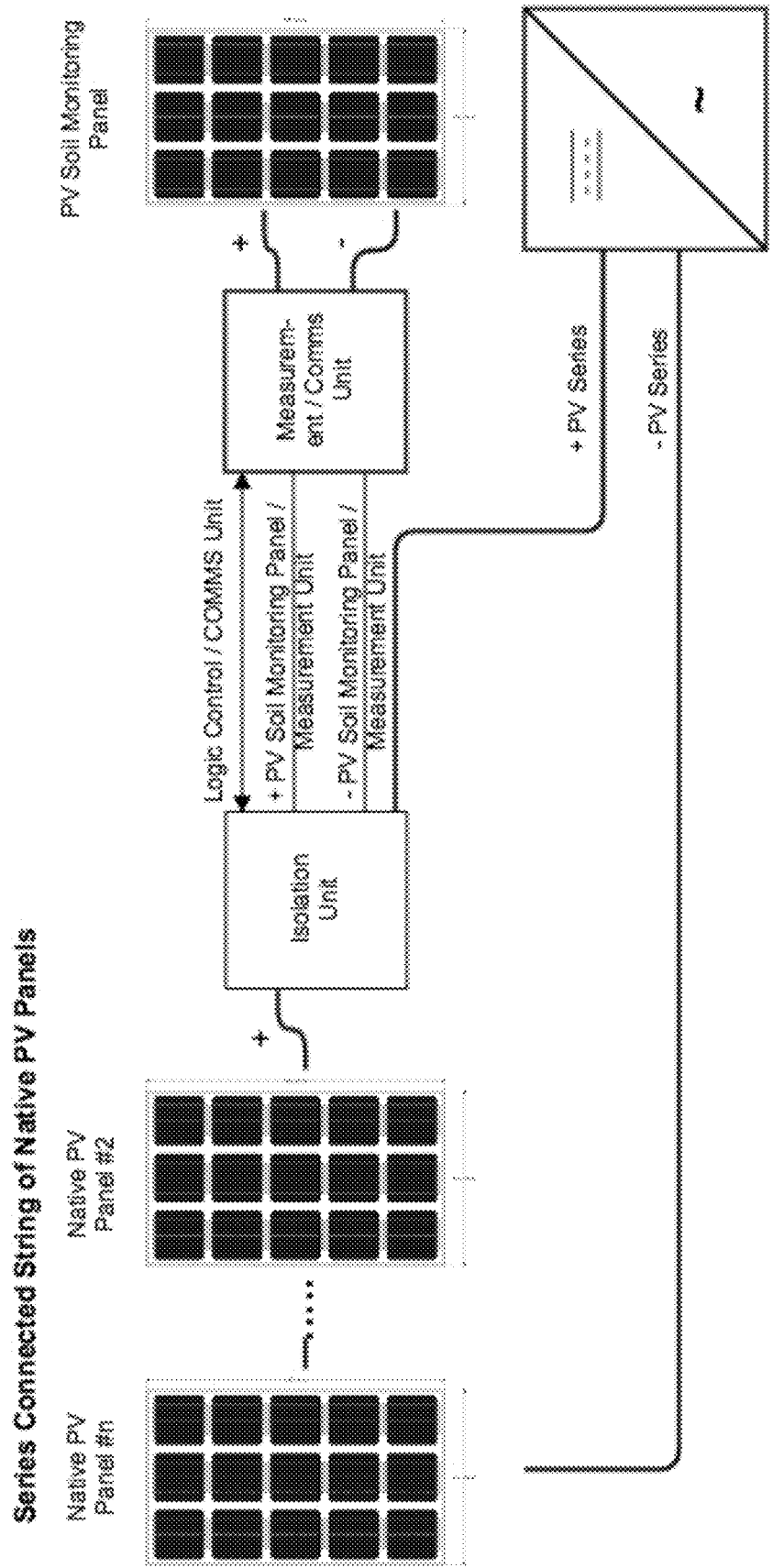
Figure 8B:
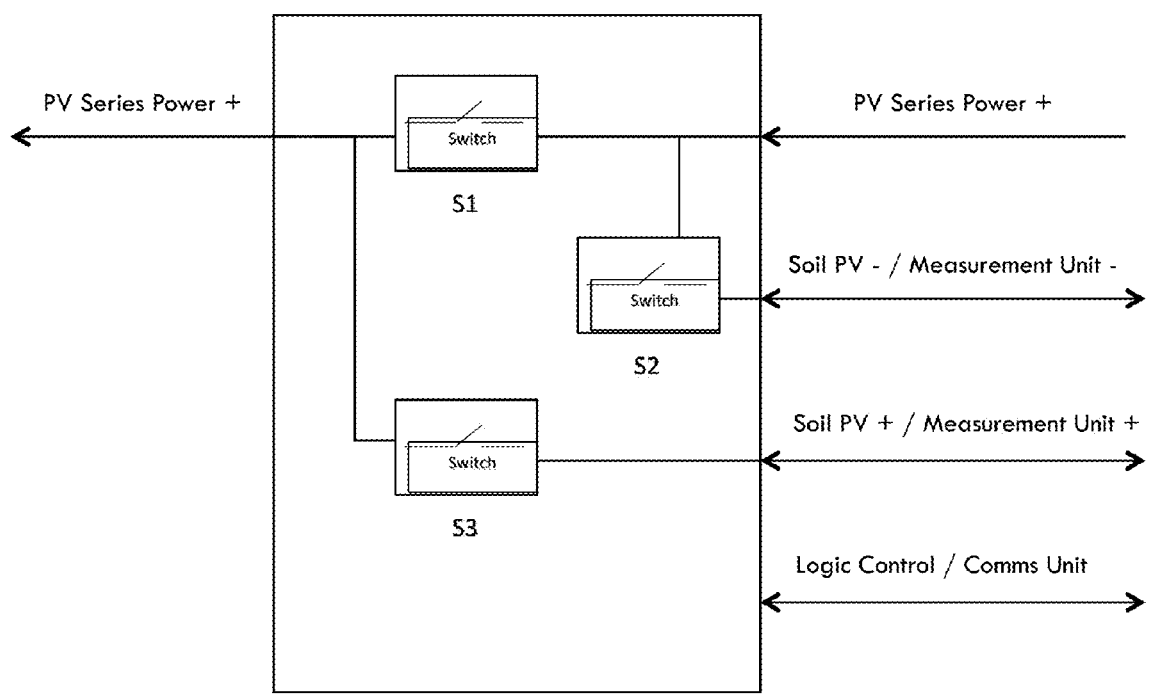
Figure 9:
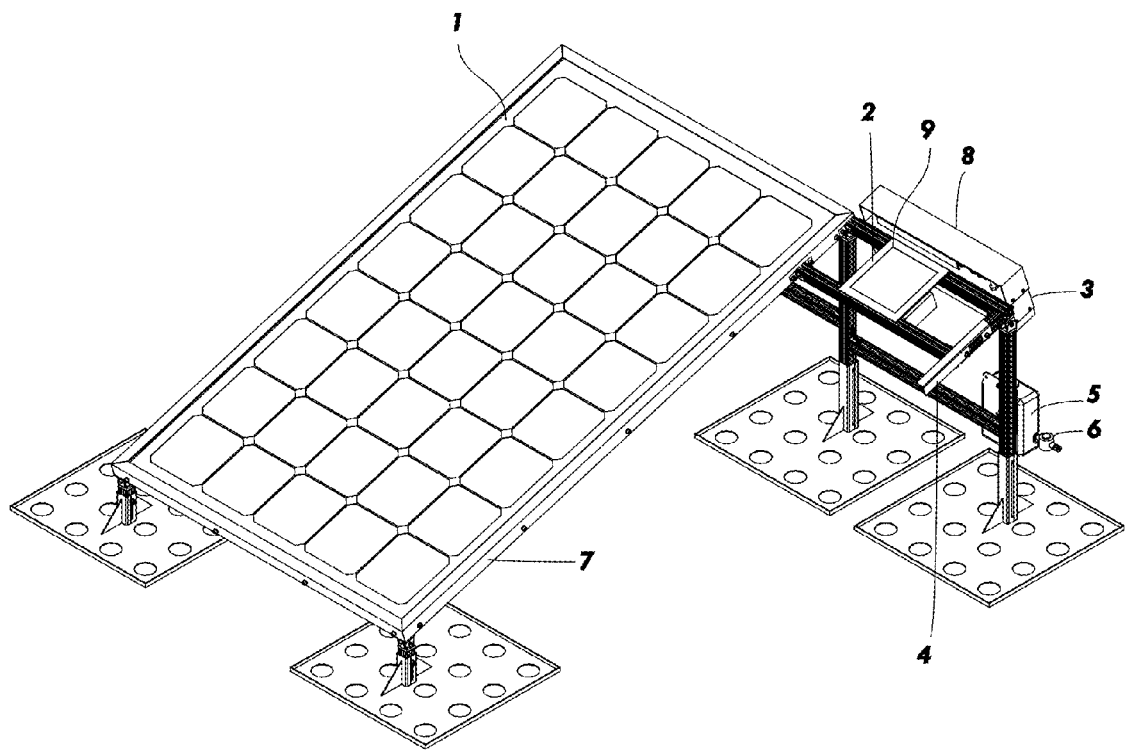
Figure 10A:
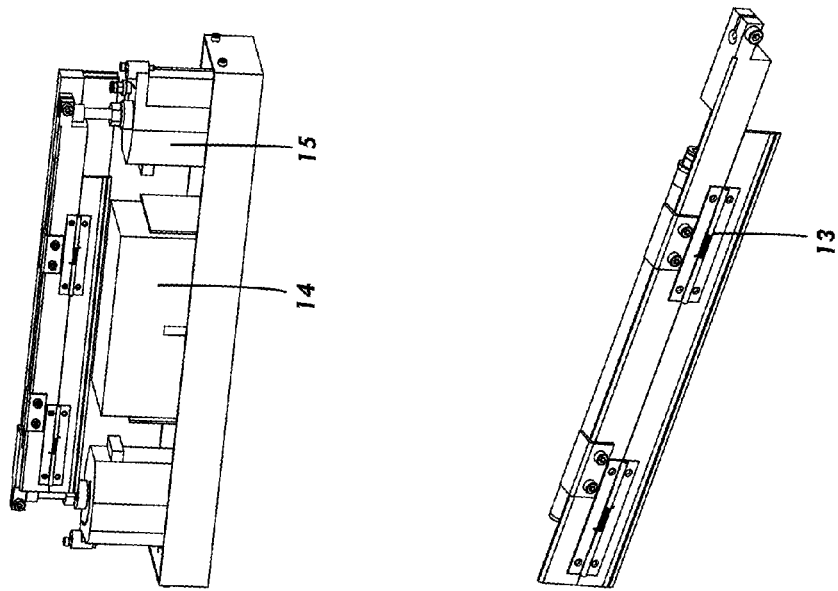
Figure 10A:
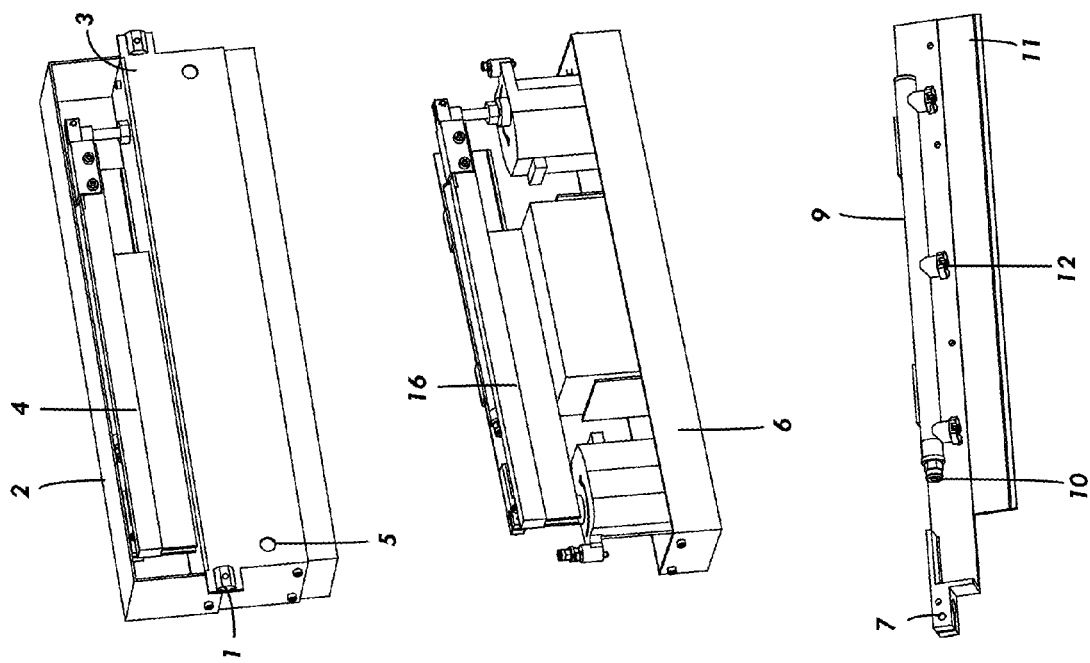
Figure 10B:
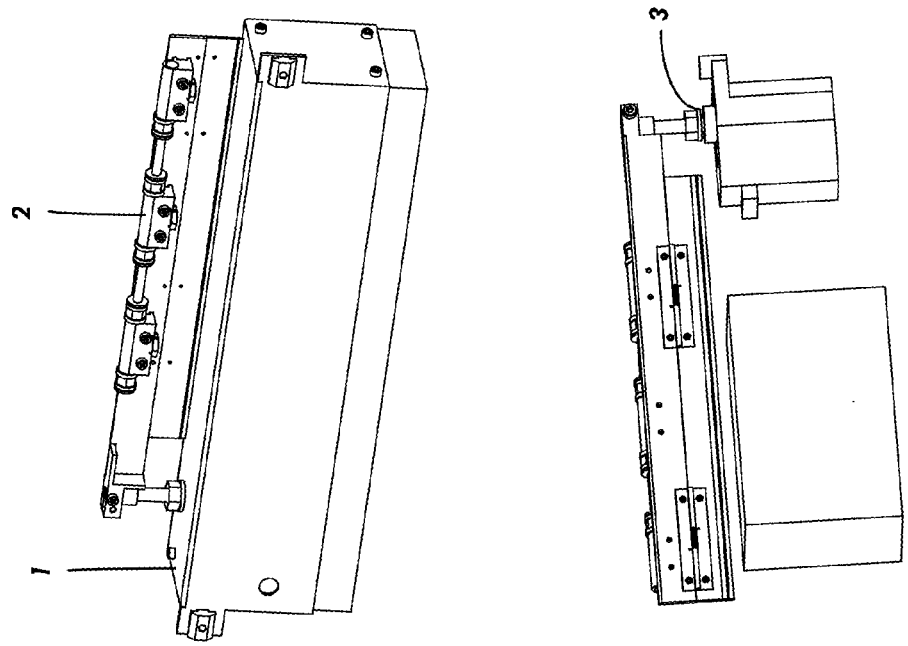
Figure 10B:
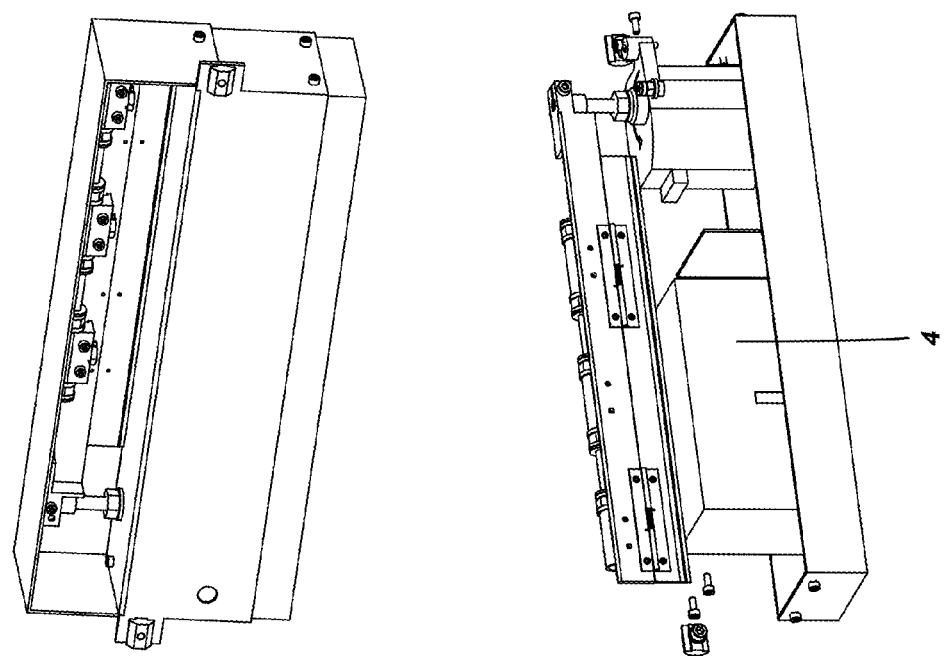
Figure 11:
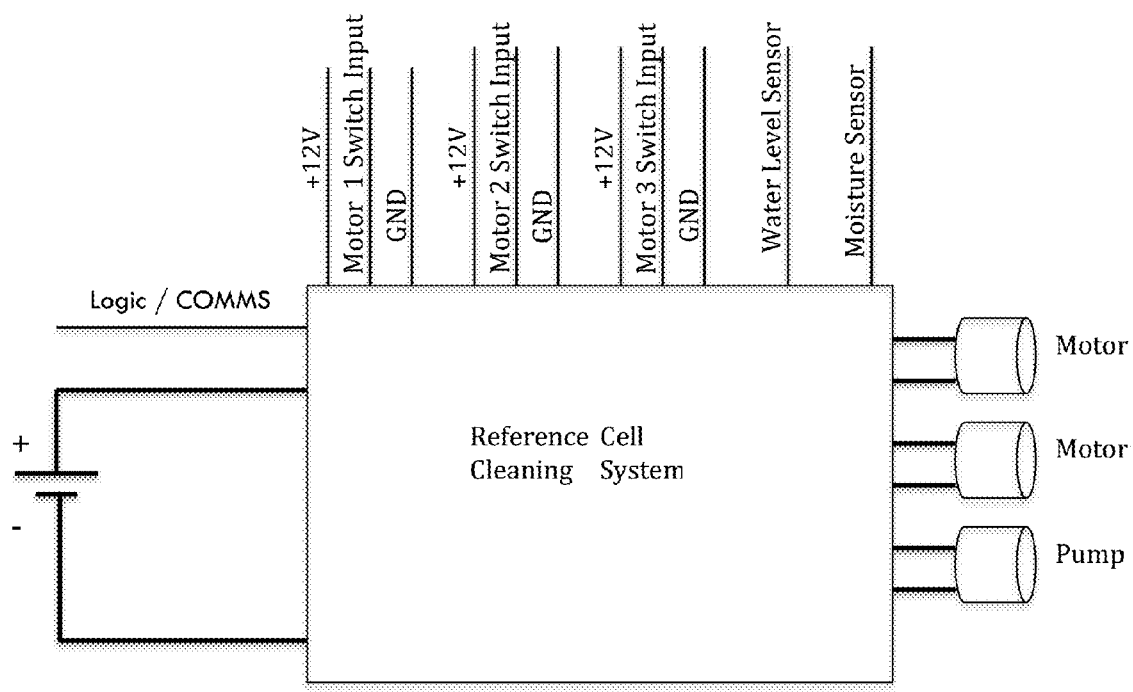
Figure 12:
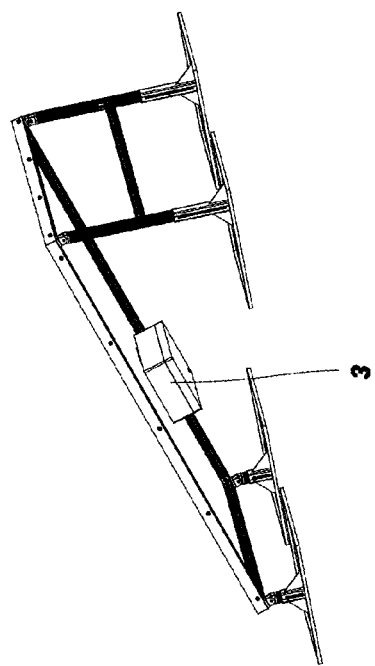
Figure 12:
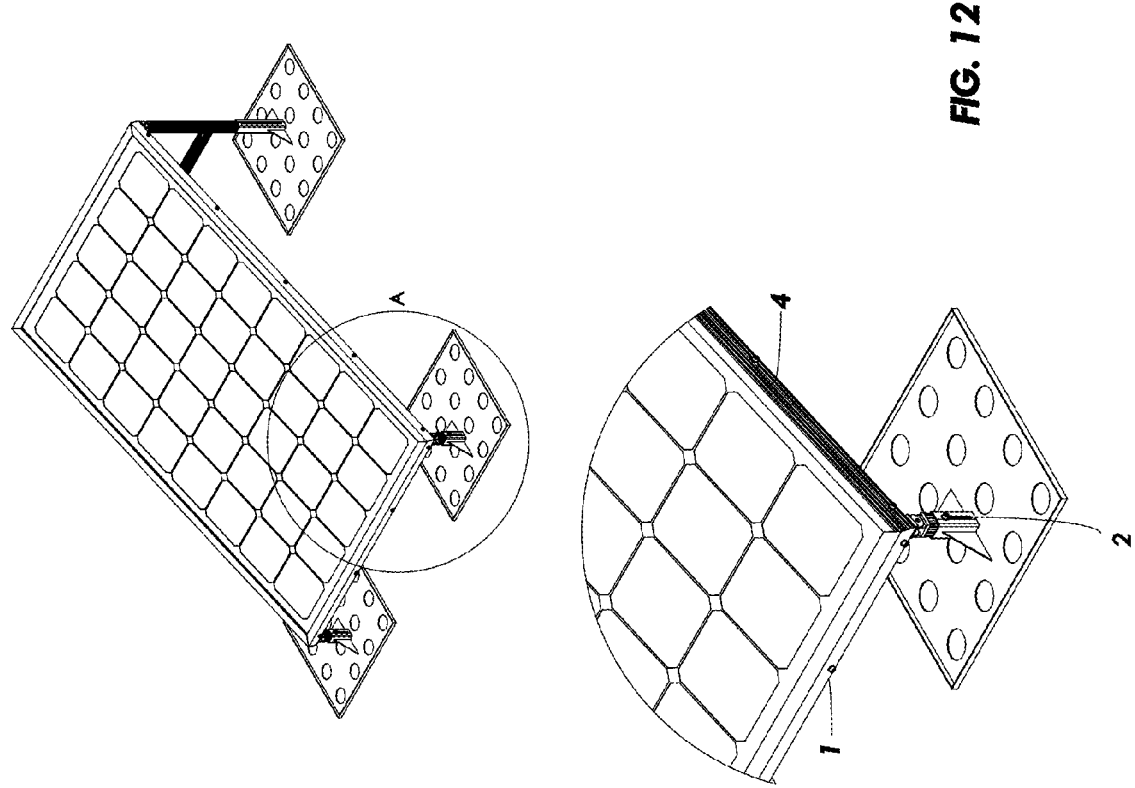
Figure 13:
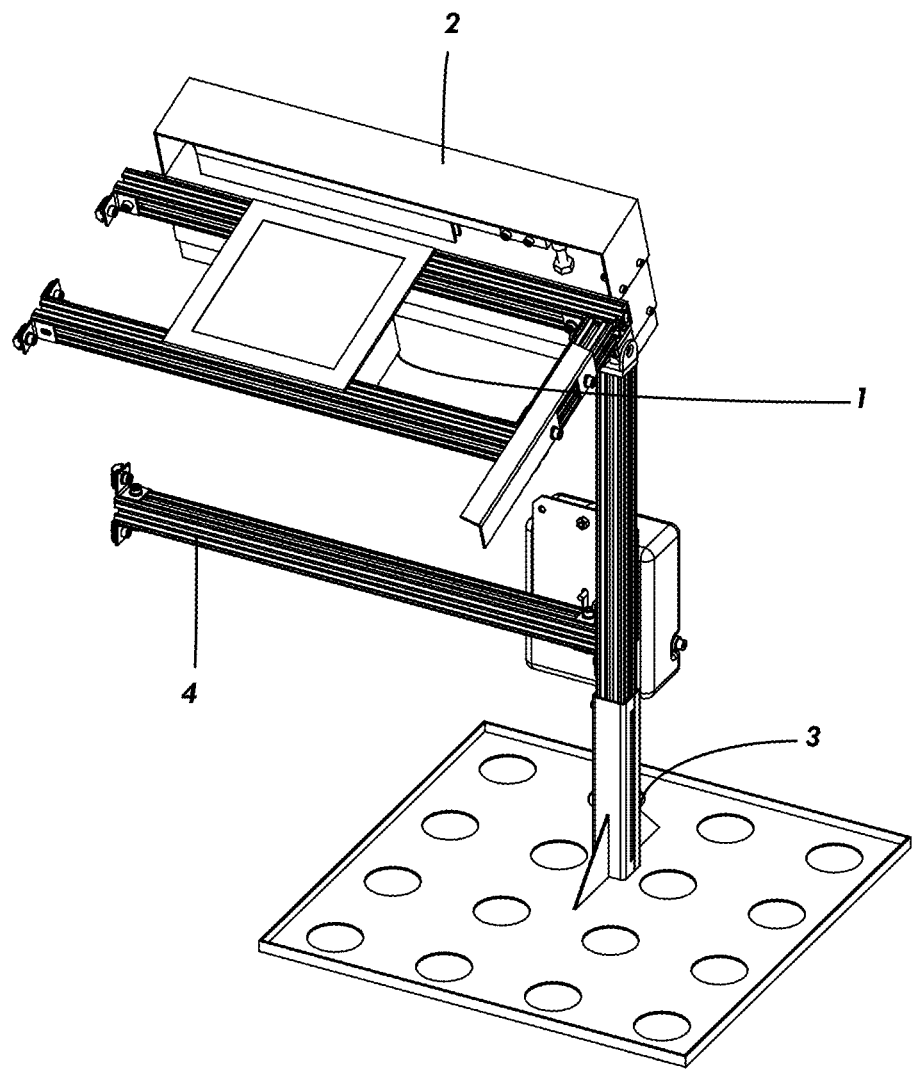
Figure 14:
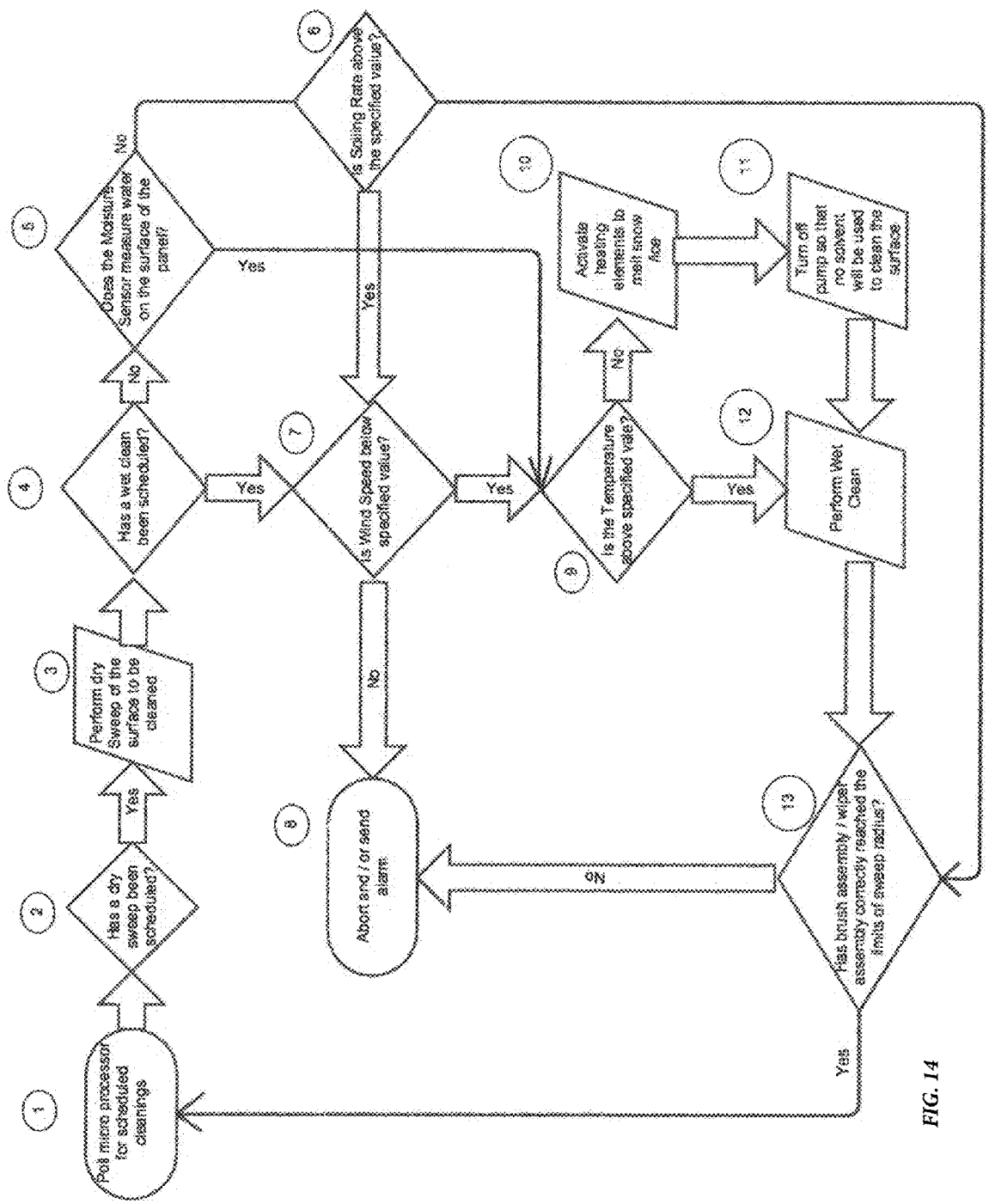

FIB. 7B shows a block diagram of the Communications Unit for the Reference panel;

FIG. 8A shows a block diagram of the Bypass Switch as it is connected inside the PV array. This is an accessory that may or may be included as an optional feature providing a means for measuring the soiling level on any PV panel within a PV array;

FIG. 8B shows a block diagram of the Bypass switch circuit;

FIG. 9 shows a Soil Monitoring Panel with Reference Panel and Cleaning System;
1. Soil Monitoring Panel
2. Reference Panel
3. Motor Enclosure
4. Self Cleaning Bar
5. Cleaning Solution Tank
6. Cleaning Solution Pump
7. Detachable Mounting Frame
8. Motor Enclosure Cover
9. Moisture Sensor mounted on Reference Panel FIG. 10A shows a design of an two motor cleaning system with motor enclosure that houses and protects the motors and battery. This system also provides a cover for protecting the Brush and Squeegee tools from environmental elements;
1. Mounting Brackets
2. Protective Cover
3. Top of Motor Enclosure
4. Dry Brush
5. Cable entry
6. Bottom of Motor Enclosure
7. Motor Axle Mounting Bracket
8. Squeegee Mounting Arm
9. Spray Manifold with Spray Nozzles
10. Cleaning Solution Enters Spray Manifold
11. Squeegee blade
12. Spray Nozzles
13. Optional Spring Hinge Connects Squeegee Arm with Blade
14. Battery
15. Wiper Motor
16. Brush FIG. 10B shows a design of a one motor cleaning system with motor enclosure that houses and protects the motors and battery.
1. Motor enclosure
2. Spray Manifold
3. Single Motor System
4. Battery FIG. 11 shows a cleaning system control unit block diagram;

FIG. 12 shows a framing system for the Soil Monitoring panel. The system provides a method to mount the Soil Monitoring panel as well as easily change the frame to match the same boarder distance as any pv panel;
1. Outside Frame holds PV panel to Aluminum supporting structure
2. Adjustment slots for adjusting height/angle of Soil Monitoring Panel
3. Electronics Enclosure mounted to back of Soil Monitoring Panel
4. Aluminum Supporting Structure FIG. 13 shows an automatic cleaning system which can be mounted onto the mounting structure of the Soil Monitoring Panel or may be mounted onto any standard pv mounting structure;
1. Electronics Enclosure mounted onto Reference Panel
2. Motor Enclosure
3. Adjustable slots for adjusting height/inclination angle of Reference panel
4. Supporting structure mounts onto any adjacent structure
5. Water tank+Water pump+Level Sensor
6. Cleaning Bar FIG. 14 shows a Cleaning System Flow Chart—Figure describes the program for cleaning the Reference Panel;
1. Microprocessor of Communications unit sends signal to initiate cleaning
2. Has dry sweep been scheduled? Yes: 3
3. Perform Dry sweep
4. Has wet clean been scheduled? No: 5, Yes: 7
5. Does Moisture sensor measure water on surface of Ref panel? No: 6, Yes: 9
6. Is Soiling Rate above specified value? No: 13, Yes: 7
7. Is windspeed below specified value? NO: 8, Yes: 9
8. Abort and/or send alarm
9. Is the temperature above specified value? No: 10, Yes: 12
10. Activate heating elements
11. Turn off pump
12. Perform Wet clean
13. Has brush assembly/wiper correctly reached the limits of its radius? No: 8, Yes: 1

Figure 15:
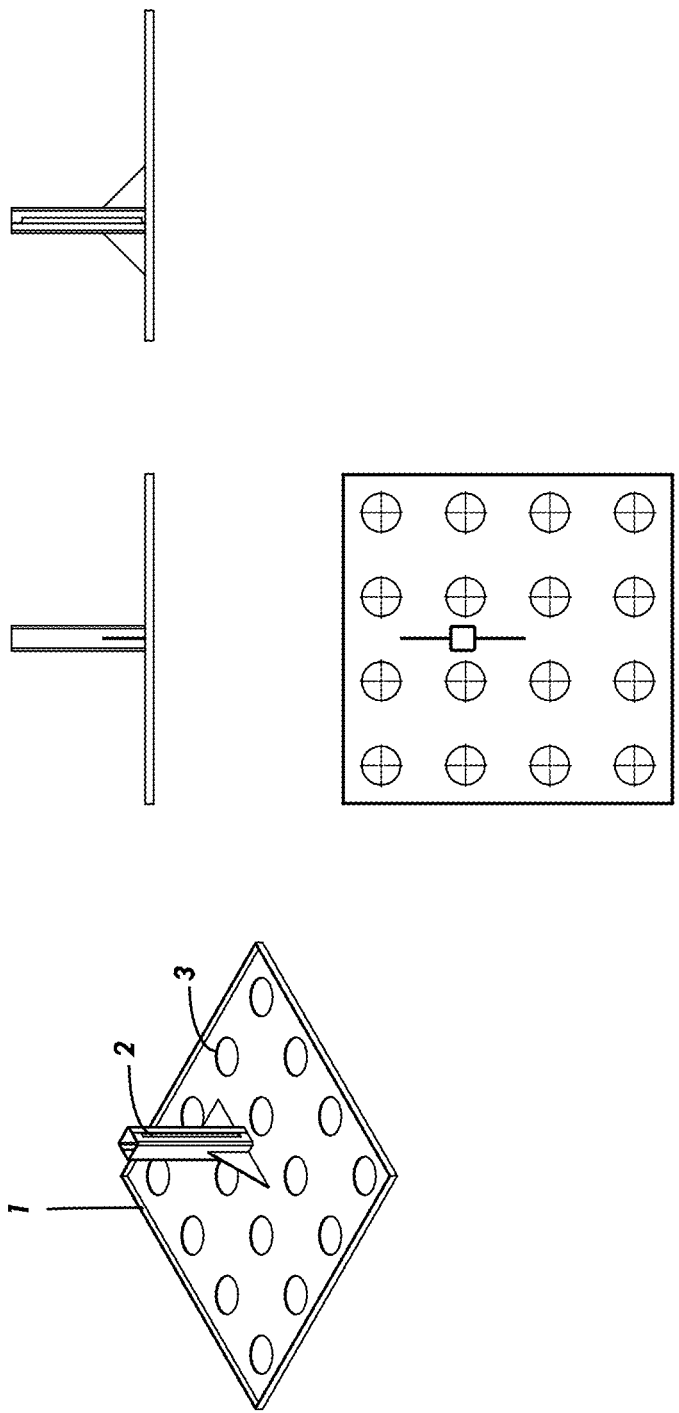
Figure 16:
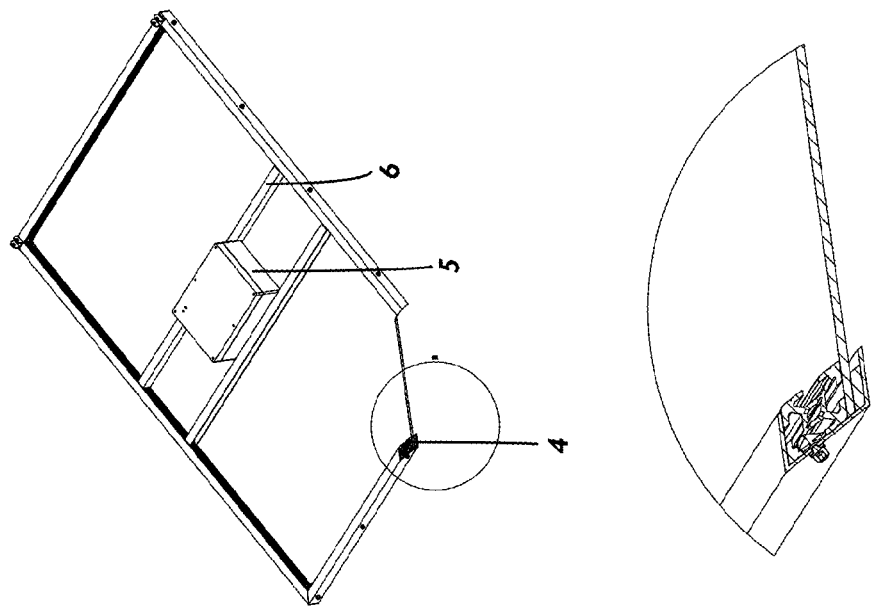
Figure 16:
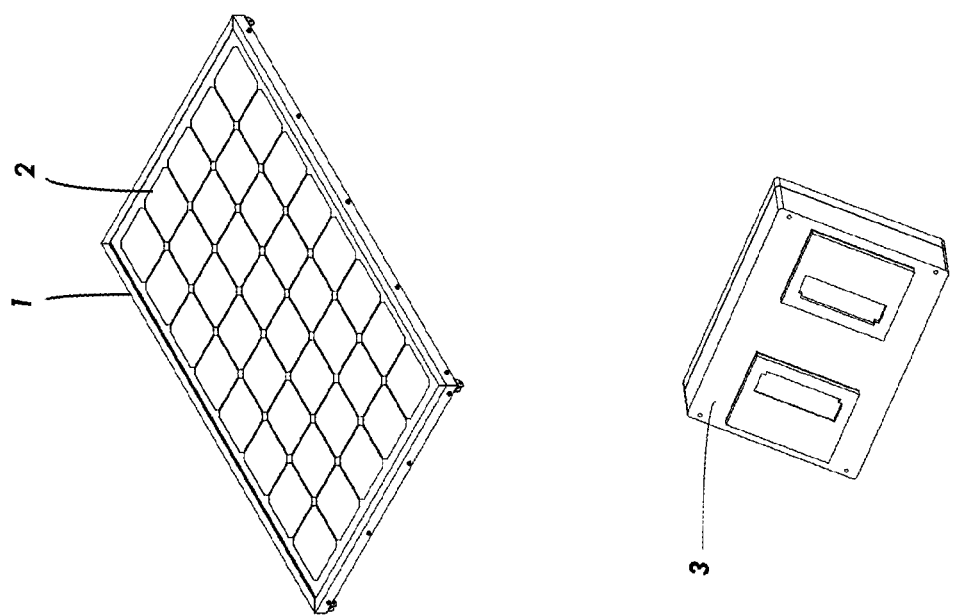

FIG. 15 shows Adjustable Base Mounts. This figure shows the base feet design that support the Soil Monitoring Panel and/or the Reference Panel and Cleaning System; and
1. Ridged Border to Keep Ballast in-place
2. Leg Mount with Sliding Holes for Adjustable height
3. Drainage holes
4. Reinforced Supports FIG. 16 shows a Soil Monitoring panel with mounted Electronics enclosure and adjustable frame system.
1. Adjustable Framing System
2. Soil Monitoring Panel 3. Electronics Enclosure with Junction Box
4. Aluminum Profiles attach to frame
5. Electronics enclosure attaches to Soil Monitoring Panel
6. Aluminum Profiles provide Mechanical Support for Electronics Enclosure

DETAILED DESCRIPTION

Various terms used herein are intended to have particular meanings. Some of these terms are defined below for the purpose of clarity. The definitions given below are meant to cover all forms of the words being defined (e.g., singular, plural, present tense, past tense). If the definition of any term below diverges from the commonly understood and/or dictionary definition of such term, the definitions below control.

At the outset, it should be understood by one of ordinary skill in the art that embodiments of the present solar panel soiling monitoring system can include software or firmware code executing on a computer, a microcontroller, a microprocessor, or a DSP processor; state machines implemented in application specific or programmable logic; or numerous other forms. The present solar panel soiling monitoring system can include one or more computer programs, which include non-transitory machine-readable media having stored thereon instructions that can be used to program a computer (or other electronic devices) to perform processes according to the presently claimed solar panel soiling monitoring system. The machine-readable media can include, but is not limited to, floppy diskettes, optical disks, CD-ROMs, and magneto-optical disks, ROMs, RAMs, EPROMs, EEPROMs, magnetic or optical cards, flash memory, or other type of media or machine-readable medium suitable for storing electronic instructions.

Figure 1:
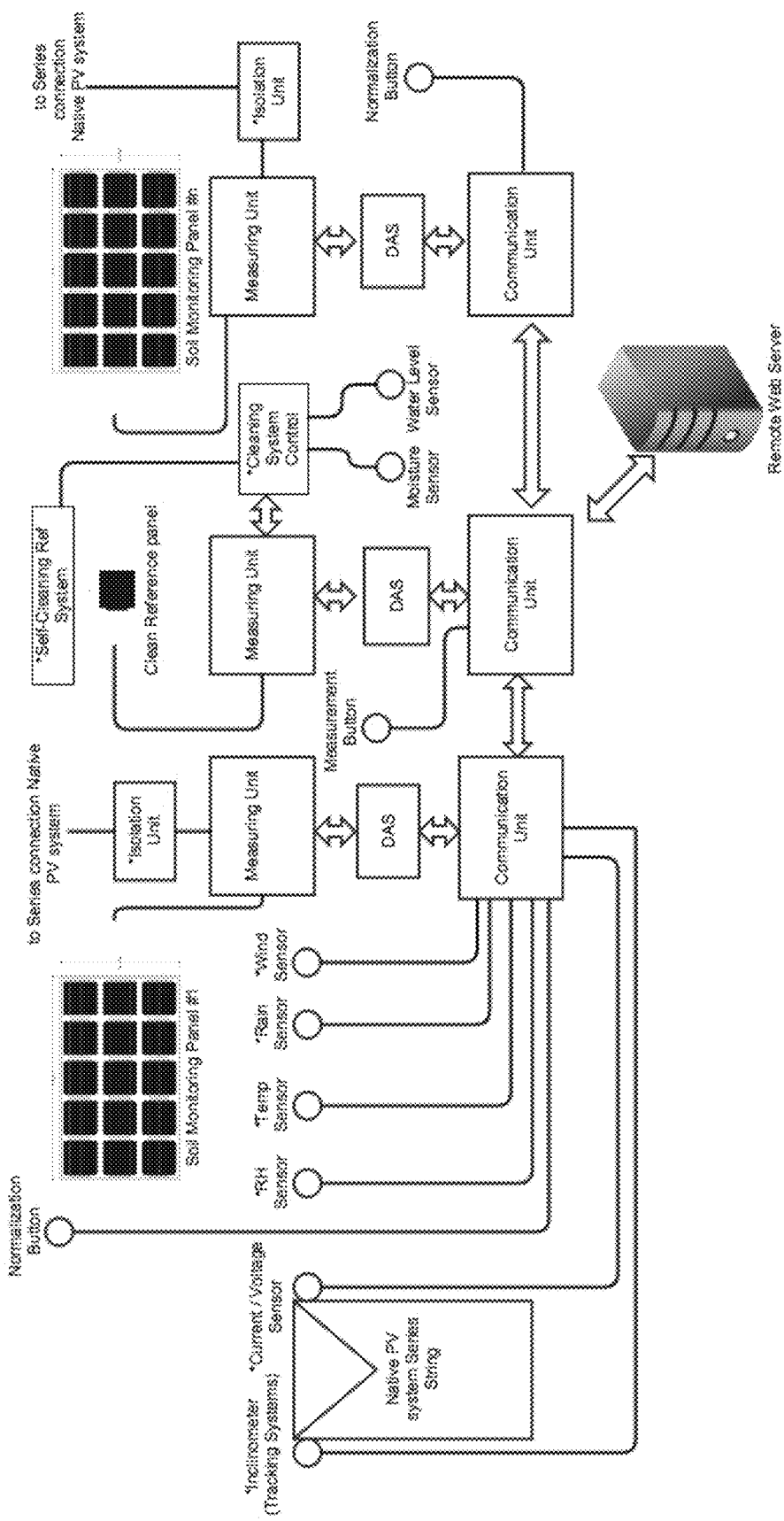
FIG. 1 shows a schematic diagram of a solar panel soiling monitoring system according to the present invention.

Referring to FIG. 1, the solar panel soiling monitoring system (1, 6A, 6B) includes a clean Reference solar panel (1, 6A, 6C) having an automated cleaning system (FIG. 1, 9, 10, 11, 13). A Soil monitoring solar panel (1, 6A, 6B) is used to provide measurements of a soiled panel versus the clean reference (1, 6A, 6C). Cleaning system control units (FIG. 11, 15) are connected to the Automated cleaning system (FIG. 1, 9, 10, 11, 13), which comprise a water tank, brush and/or squeegee assemblies. The solar Soil Monitoring panels (1, 6A, 6B) and cleaning system control units (FIG. 11) are connected to a measurement unit (FIG. 1, FIG. 2A, FIG. 2B, FIG. 6A) which provides measurement of the Isc of each cell of the Soil Monitoring panel (1, 6A, 6B) individually and in coordination with the measurement of the Isc of the corresponding Reference cell (1, 6A, 6C) The Measurement Unit (FIGS. 1, 2A, 2B, 6A,) of the Soil Monitoring Panel (1, 6A, 6B) and Reference panel (1, 6A, 6C) are connected to one or more Data Storage System (FIGS. 1, 2A, 2B, 7A, 7B) s (ie. EEPPROM). The Measurement Unit (FIGS. 1, 2A, 2B, 6A), is also connected to a communications unit (FIG. 1, 7A, 7B). The data storage unit may be a separate third party system (ie. Data Acquisition System) consisting of a storage and control system or may be integrated into the measurement (FIGS. 1, 2A, 2B, 6A) and/or communications units (FIG. 1, 7A, 7B).

A number of environmental sensors including a relative humidity sensor a temperature sensor, a rain sensor, moisture sensor and a wind sensor may be connected to the communications (FIG. 1, 7A, 7B), motor control and or measurement units (FIGS. 1, 2A, 2B, 6A).

Additionally, a current/voltage sensor connected to the native PV system (FIG. 1), is also connected to the measurement unit (FIGS. 1, 2A, 2B, 6A) to relay current/voltage information about the native PV system to the communications unit (FIG. 1, 7A, 7B) A normalization button (FIG. 1) is connected to the communications unit (FIG. 1, 7A, 7B) of the Soil Monitoring Panel (FIG. 1, FIG. 6A, FIG. 6B) to recalibrate measurements to a normalized form after each cleaning of the PV system. The Communications unit (FIG. 1, 7A, 7B) may have a connection to a modem, which exchanges the solar panel data and calculations between a server (FIG. 1) and the local Data Storage System (FIGS. 1, 2A, 2B, 7A, 7B) s. While the server (FIG. 1), may be remote, the remainder of the system, is considered to be located on the site where the PV system losses are to be measured.

Soil Monitoring Panels

Traditional methods to measure loss of energy due to soiling of the PV system include measuring a combination of voltage and current for a specified pv panel or panels in reference to a clean pv panel. However, due to the fact that standard PV panels consist of a plurality of series-connected PV cells these measurements are limited in accuracy and are lacking in the detailed analysis of the patterns of soiling in a PV system. Alternative methods have been developed to measure soiling levels by measuring the differences in current and voltage on two single cell pv reference panels. However these methods lack the characteristic effects of soiling that are specific to a PV panel consisting of a plurality of cells mounted inside a standard PV module. The present invention seeks to solve this problem by connecting each cell of a standard PV module to a Measurement Unit (FIGS. 1, 2A, 2B, 6A), whereby the Isc of each cell can be measured individually in addition to the MPP of the series connected cells.

The soil monitoring panel (FIG. 1, FIG. 6A, FIG. 6B) may include a standard frame proportional to those of standard solar panels. The Reference panel (FIG. 1, FIG. 6A, FIG. 6C), e.g., clean reference solar panel (FIG. 1, FIG. 6A, FIG. 6C) may be without a frame to enable easy cleaning by the automated cleaning system (FIG. 1, 9, 10, 11, 13)

Figure 6B:
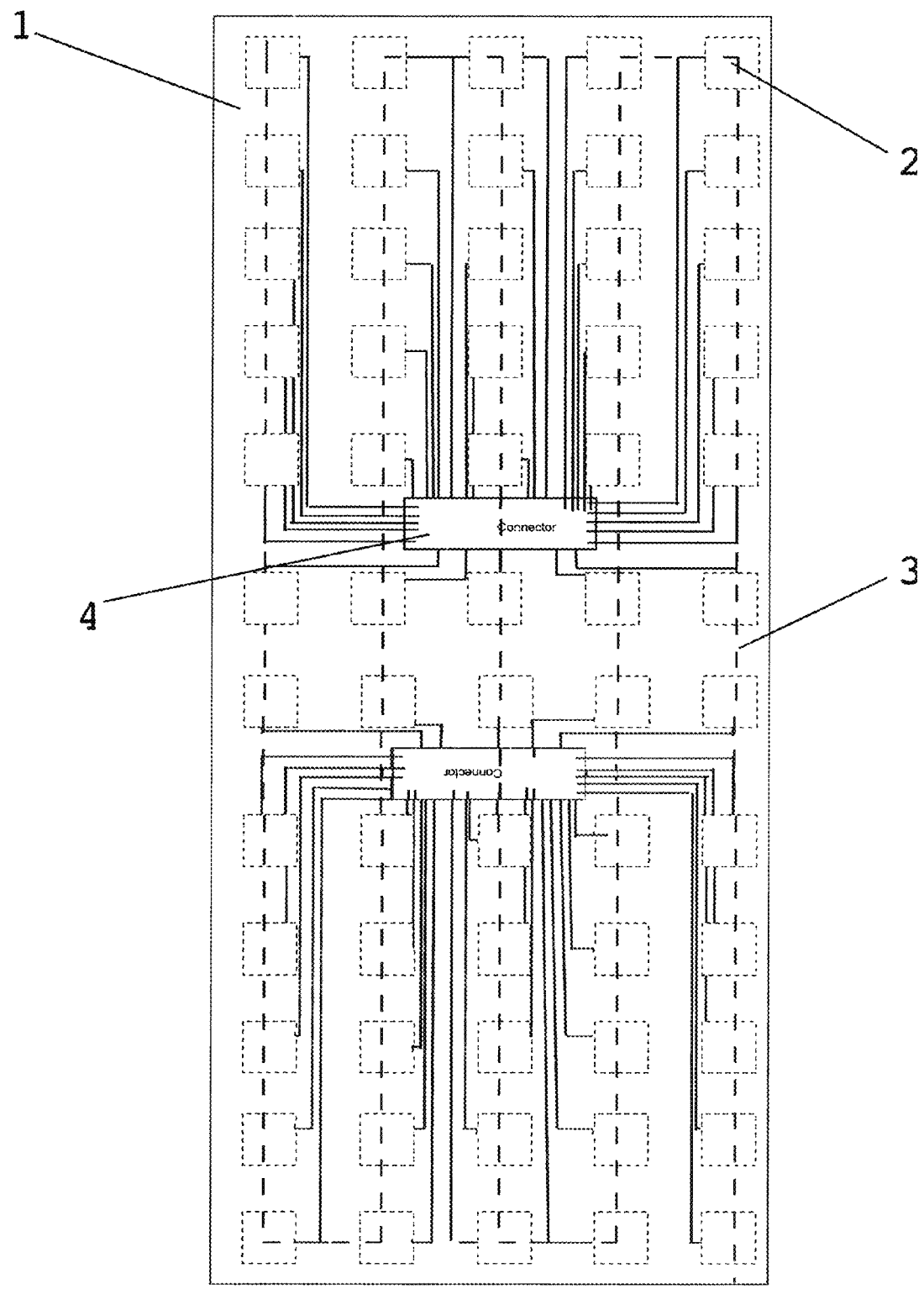
FIG. 6B shows a block diagram showing the Flexible PCB which is used to connect the PV cells of the Soil Monitoring panel or Reference Panel to the Measuring unit, by providing a an additional circuit superimposed on the existing series connected pv cells. This example shows 30 cells but any number of cells can be connected;
1. Flexible PCB
2. Wire Traces Connect to PV Cells below the Flex PCB
3. Series Power Connection below Flex PCB
4. Connectors to Measurement Unit/Comms Unit
Figure 7A:
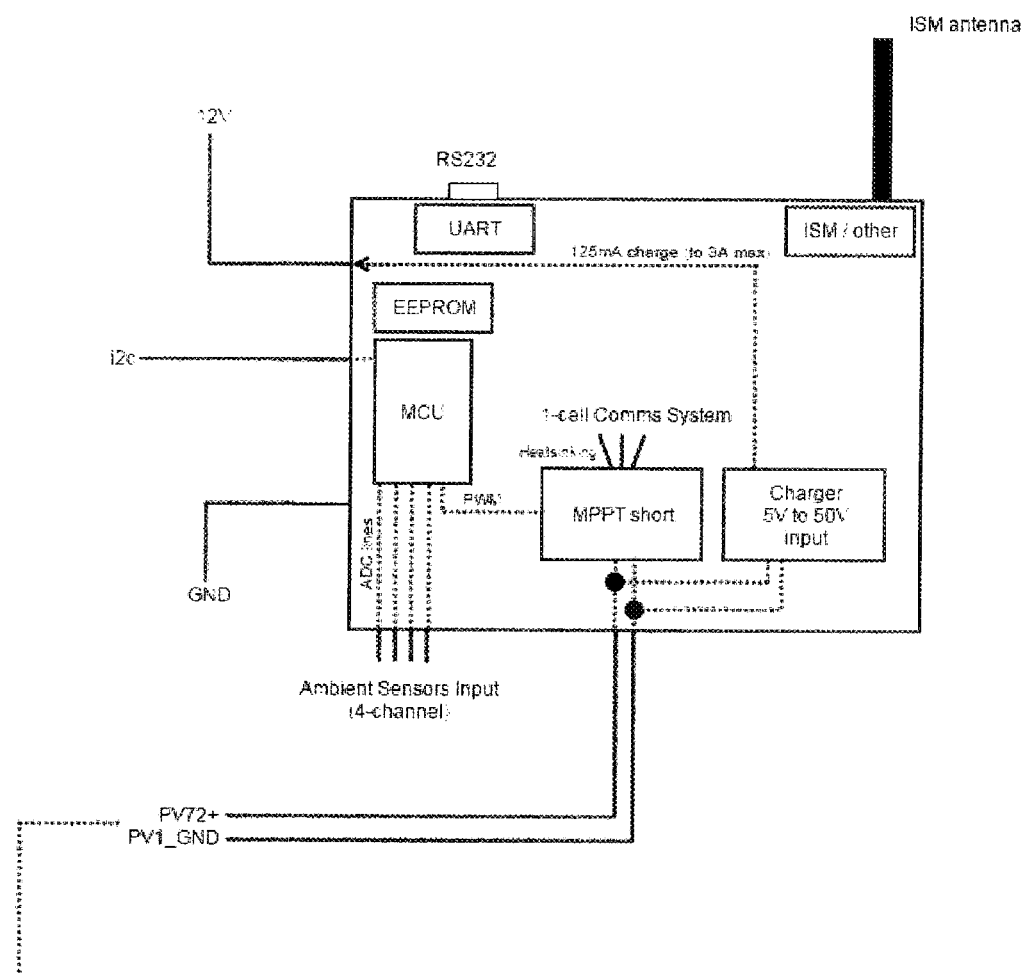
FIG. 7A shows a block diagram of the Communications Unit for the Soil Monitoring Panel.
Figure 7B:
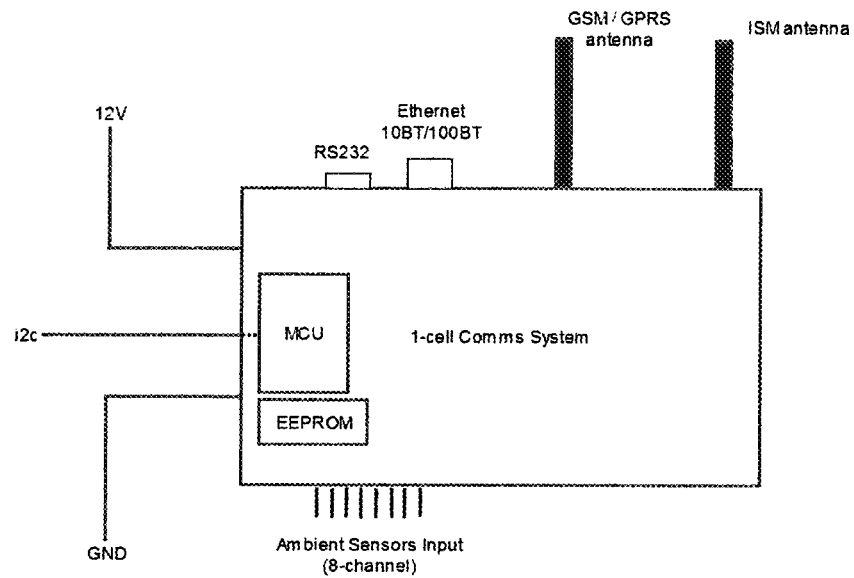

The current of a PV panel is directly proportional to the irradiance incident on the surface of the cells. As standard PV panels consist of a plurality of cells wired in-series, the current of the PV panel is limited to the current of the weakest cell in the series connected string of cells. In order to accurately measure losses due to soiling, and better understand the specific losses due to pattern soiling it is important to measure the short circuit current of each cell individually as it is situated inside the PV panel. It is impossible to determine the pattern of soiling present on a PV panel by measuring the current of a Standard series connected PV panels. In addition, normalization is complicated by the PV cell mismatch which can lead to substantial errors in measurement on a standard PV panel. By connecting each cell of the Soil Monitoring panels (FIG. 1, FIG. 6A, FIG. 6B) to a Measurement Unit (FIGS. 1, 2A, 2B, 6A), the mismatch between cells can be eliminated, significantly improving the accuracy of the soiling loss measurements. Additionally soil patterns can be easily assessed to determine the specific soiling losses and suitable cleaning techniques. As shown in FIG. 6A, cells of the Soil Monitoring Panels (FIG. 1, FIG. 6A, FIG. 6B) are connected individually to the Measurement Unit (FIGS. 1, 2A, 2B, 6A,) (which may be on the back of the panel or in a separate enclosure)

The cells of the Soil Monitoring panels (FIG. 1, FIG. 6A, FIG. 6B) are also connected in-series to provide power to the charger as well to measure the MPP of the series connected cells.

Measurement Unit

Figure 2A:
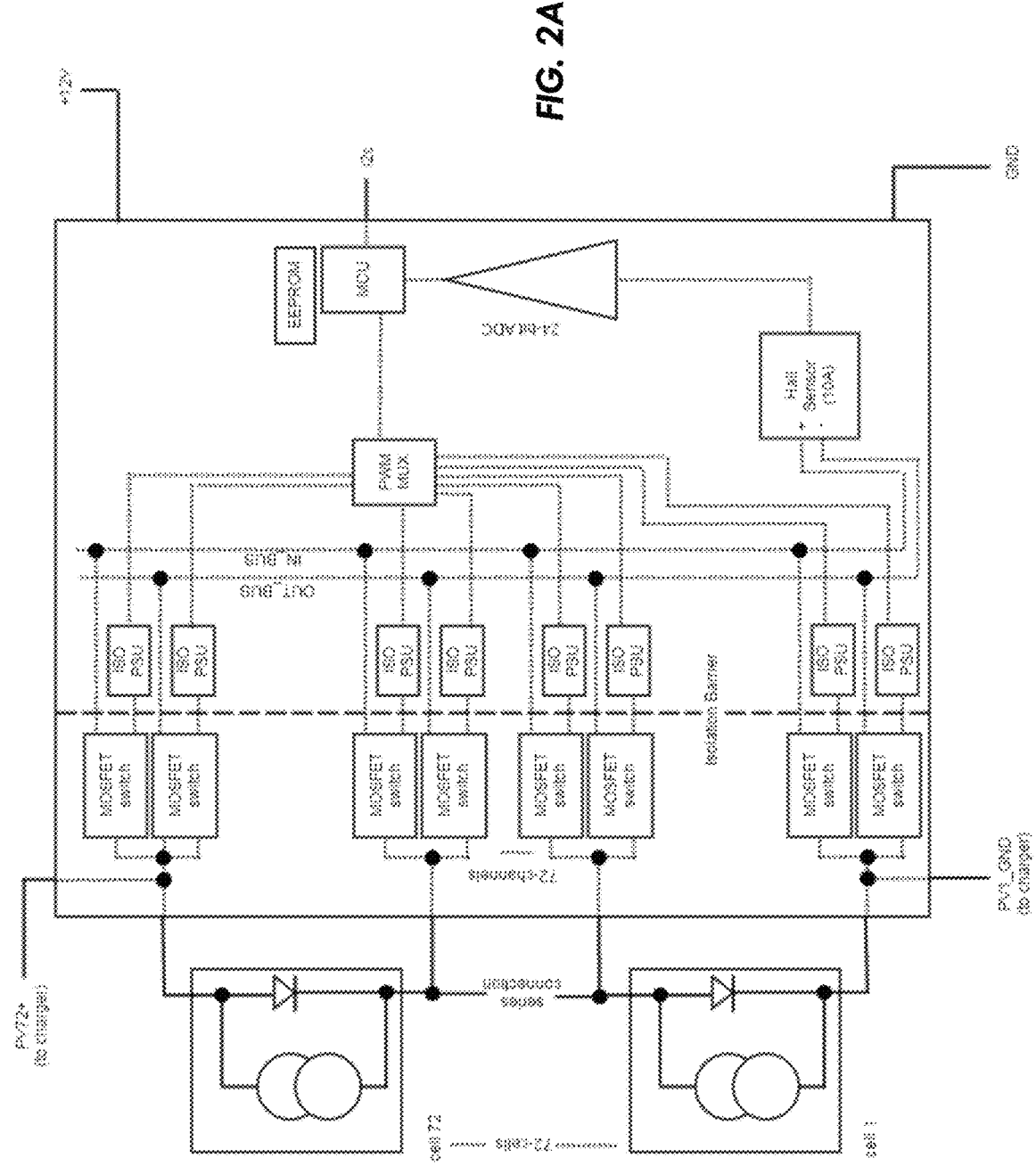
FIG. 2A shows a block diagram of a Measurement Unit of the Soil Monitoring panel. In this example there are 72 channels for measuring short circuit current of up to 72 individual PV cells, however, any number of cells may be measured by adding or subtracting channels.
Figure 2B:
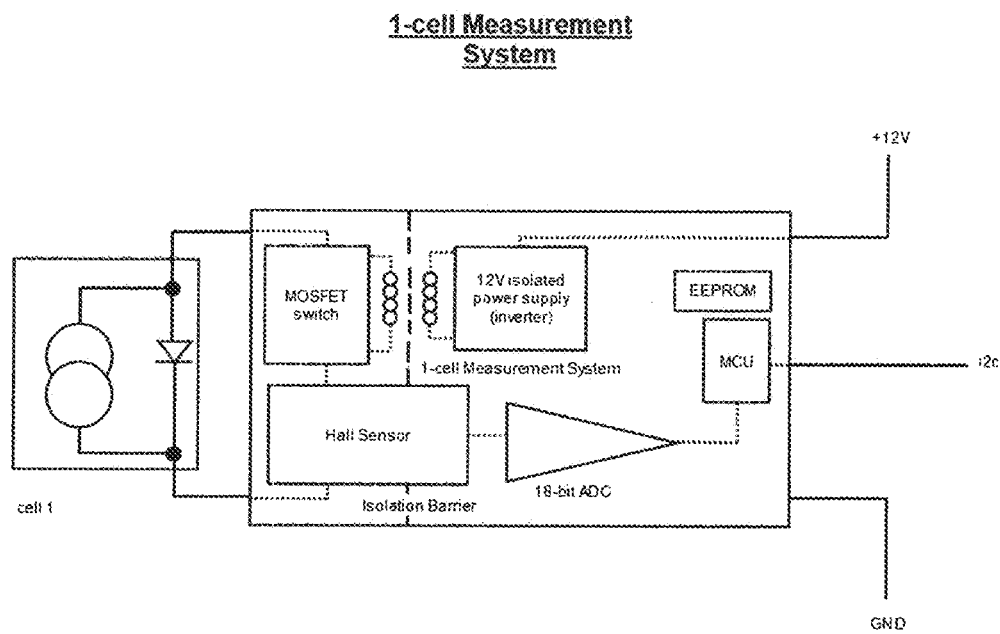
FIG. 2B shows a block diagram of a Measurement Unit for the Reference Panel. In this example there is only 1 channel for measuring short circuit current of 1 pv cell, however, any number of cells may be measured by adding channels.
Figure 6C:
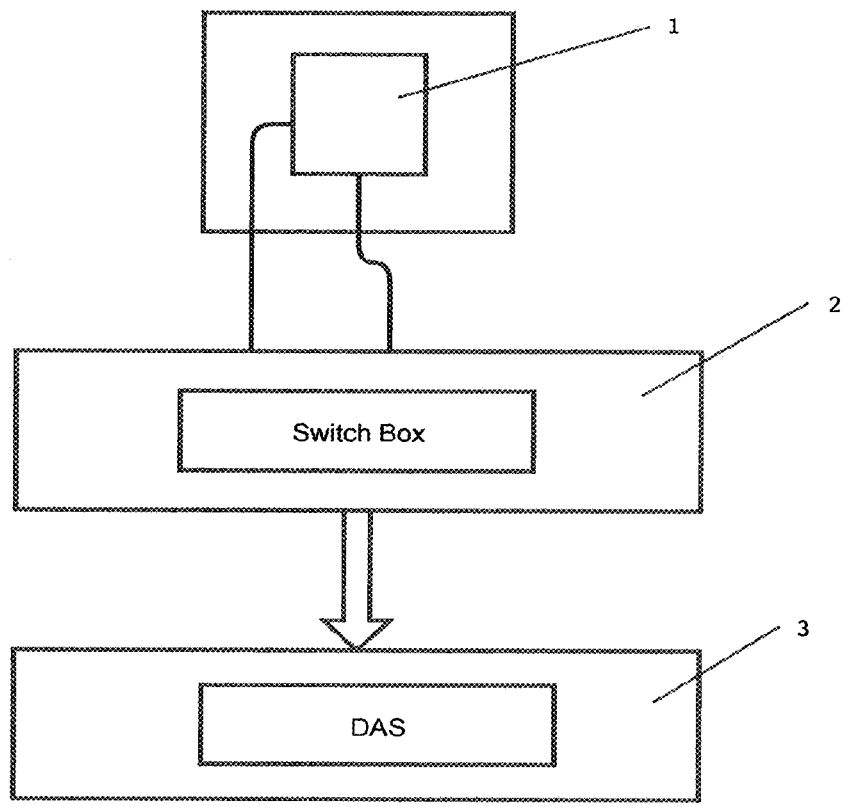
FIG. 6C shows a block diagram of single cell Reference Panel. This example shows 1 pv cell but any number of cells can be connected;
1. Reference Panel/PV Cell
2. Measurement Unit with Switch Box
3. Communications Unit with Data Storage System

With Respect to the measurement unit (FIGS. 1, 2A, 2B, 6A), a minimum of two panels of the type described above (one soil monitoring panel (FIG. 1, FIG. 6A, FIG. 6B) and one reference panel (FIG. 1, FIG. 6A, FIG. 6C) are measured simultaneously. Each panel of the Soil Monitoring System (Soil Monitoring Panel and Reference Panel) may be connected to a single measurement unit (6A) or each panel may be connected to a separate measurement unit ((FIGS. 1, 2A, 2B, 6A), dedicated to measuring the Isc of each panel. In one embodiment, the Measurement Unit (FIGS. 1, 2A, 2B, 6A), is located in the junction box of the panel. In another embodiment, the Measurement Unit (FIGS. 1, 2A, 2B, 6A), is provided as a separate unit (in a separate enclosure). Each cell of each panel will be connected from the junction box of the panel to the Measurement Unit (FIGS. 1, 2A, 2B, 6A,). A switching circuit inside the measurement unit will connect the measurement devices to each cell in the Soil Monitoring panel and Reference panel. The measurement unit (FIGS. 1, 2A, 2B, 6A), will measure the individual short circuit current (Isc) from each cell in the soil monitoring panel (FIG. 1, FIG. 6A, FIG. 6B) to the corresponding cell or cells in a clean reference panel (FIG. 1, FIG. 6A, FIG. 6C). The Measurement Unit (FIGS. 1, 2A, 2B, 6A) includes a microprocessor (MCU) (FIG. 2A, 2B) in operable communication with analog-to-digital converter (FIG. 2A, 2B) multiplexer (FIG. 2A, 2B) MOSFET transistors (FIG. 2A, 2B) and precision Hall sensors (FIG. 2A, 2B). In one embodiment of the Measurement Unit (FIGS. 1, 2A, 2B, 6A), a Data Storage System (FIGS. 1, 2A, 2B, 7A, 7B) or data acquisition system (FIG. 1) having a memory unit will be included on the same printed circuit board (PCB) as the switching circuits. In another embodiment, any third party Data Storage System (FIGS. 1, 2A, 2B, 7A, 7B) or DAS can be connected to the Measurement Unit (FIGS. 1, 2A, 2B, 6A), as a separate unit.

Using these components, the measurement unit (FIGS. 1, 2A, 2B, 6A), upon a pulse signal from the communications unit (FIG. 1, 7A, 7B) on a periodic basis (e.g., one time per hour), automatically takes the instantaneous short circuit current Isc) measurements from each corresponding pair of cells from the soil monitoring panel (FIG. 1, FIG. 6A, FIG. 6B) and the clean reference panel (FIG. 1, FIG. 6A, FIG. 6C) In another embodiment, a switching circuit in the measurement unit (FIGS. 1, 2A, 2B, 6A), can configure the cells in any combination of physical circuits (series and parallel) and measure the resulting Isc of each circuit. The Measurement Unit (FIGS. 1, 2A, 2B, 6A,) then sends the measurements to a local storage device which stores the resulting current measurements from each pair of corresponding cells from the soil monitoring panel (FIG. 1, FIG. 6A, FIG. 6B) and clean reference panel (FIG. 1, FIG. 6A, FIG. 6C) or each pair of corresponding circuits from each respective panel.

Soiling Loss Calculations

After collecting the Isc measurements from each cell of each panel, a script in the MCU of the communications unit (FIG. 1, 7A, 7B) and/or measurement unit performs a mathematical algorithm upon the individual measurements taken from each cell to determine the following (but not limited to) additional soiling characteristics, such as average soiling loss percent (average loss of all cells on soil monitoring panel (FIG. 1, FIG. 6A, FIG. 6B) vs. those on the clean reference solar panel (FIG. 1, FIG. 6A, FIG. 6C) percent of non-uniformity of soiling, (delta between the weakest cell on the soil monitoring panel and the strongest cell on the soil monitoring panel (FIG. 1, FIG. 6A, FIG. 6B) soiling losses from cells located in the corners of the panel, the loss due to soiling on each row of cells and along the borders of the panel, the total soiling loss for the panel (connected in series), and determination of any forward-biased bypass diodes.

A first program written into the MCU of the Measurement Unit (FIGS. 1, 2A, 2B, 6A), or communications unit (FIG. 1, 7A, 7B) is able to self-monitor the Soil Monitoring panels (FIG. 1, FIG. 6A, FIG. 6B) to determine if there are large differences in cell Isc values compared to other cells in the same Soil Monitoring panel. In this way, the capability exists to determine if the cells of the soil monitoring panel (FIG. 1, FIG. 6A, FIG. 6B) may have an aberration due to uncharacteristic spot soiling, such as an aberrant leaf or bird dropping, which may not be representative of the native soiling pattern in general. Using a user interface provided via the Internet web application, the user is able to configure the alarms and calculations to include or ignore these aberrations to better match the average soiling of the native PV system.

A second program written into the MCU of the Measurement Unit (FIGS. 1, 2A, 2B, 6A,) is also able to mimic the bypass diodes of the panels installed at any site. Using the Isc measurements of each cell, the microprocessor (FIG. 2A, 2B) is able to "turn off" a row of cells to mimic the specific design of the bypass diode circuitry in the native panels. In this way a close simulation of the characteristic performance of the native PV panels is maintained.

A battery and charge controller will be used to collect energy from the soil monitoring panels (FIG. 1, FIG. 6A, FIG. 6B) and/or the reference panel (FIG. 1, FIG. 6A, FIG. 6C) that is not used during the measurement process to power the Measurement Unit (FIGS. 1, 2A, 2B, 6A), electronics (MCU, ADC, MOSFETs, and the like), eliminating the need for AC power connections and facilitating completely independent and remote installation, if desired.

10-Day Clean Cycle Forecast Tool

The soiling rate will be used to update a soiling forecast tool, which will provide accurate calculations of estimated soiling losses and site-specific cleaning schedules. Front end forecast processing is shown in Table 1.0 and. Back end forecast processing described in Table 2.

TABLE 1

PV Clean Cycle Forecast Processing

| Step | Process |
|---|---|
| 1 | Input actual pv system Energy output (kWh's)/period defined*) |
| 2 | Input actual Soiling Rate from Soil Monitoring Panels (%/period defined*) |
| 3 | Input Cost of Energy ($/kWh) |
| 4 | Calculate the Amount of Energy Lost due to soiling (Actual Soiling Rate × Actual PV System Energy Output)/period defined* |
| 5 | Calculate the Cost of Energy lost due to soiling based-on the (Amount of Energy lost due to Soiling × Cost of Energy)/period defined* |

TABLE 1-continued

PV Clean Cycle Forecast Processing

| Step | Process |
|---|---|
| 6 | Calculate the Cumulative** Cost of Energy lost due to soiling by adding the current Cost of Energy Lost + the cumulative Cost of Energy Lost (Amount of Energy lost due to Soiling × Cost of Energy)/period defined* |
| 7 | Input Cost of Cleaning ($/kWp) |
| 8 | Compare the Cumulative** Cost of Energy Lost due to soiling with the Cost of Cleaning |
| 9 | Is the Cumulative** Cost of Energy Lost > the Cost of Cleaning ? No: 10, Yes 11 |
| 10 | Send alert to user (email, phone...etc) and mark Cleaning Cycle Calendar |
| 11 | Input 10 day weather forecast (rain, wind, irradiance, temp)/period defined* |
| 12 | Calculate 10 day forecast of pv system energy output based-on actual kWh/kWp and forecasted irradiance (Irr/msg/period defined*) |
| 13 | Calculate 10 day forecast Soiling rate % based-on rolling average of actual Soiling Rate determined by Soil Monitoring panel (%/period defined*) |
| 14 | Adjust 10 day Forecast Soiling Rate % by calculating additional weather factors which may increase or decrease rolling average soiling rate % based-on 10 day weather forecast |
| 15 | Calculate the 10 day forecast of the Amount of Energy Lost per period defined (Adjusted 10 day Forecast Soiling Rate * 10 Day forecast PV System Energy Output)/period defined* |
| 16 | Calculate the 10 day Forecasted Cumulative** Cost of Energy lost due to soiling per period defined, by adding the current Cumulative Cost of Energy Lost + Forecast Cumulative Cost of Energy Lost (Amount of Energy lost due to Soiling * Cost of Energy)/period defined* |
| 17 | Is the Forecast Cumulative Cost of Energy Lost > the Cost of Cleaning ? No: 1, Yes: 18 |
| 18 | Send alert to user (email, phone . . . etc) and mark Cleaning Cycle Calendar |

Additional Soil Monitoring panels (FIG. 1, FIG. 6A, FIG. 6B, FIG. 9) may also be installed at various locations on the same PV system in reference to a single clean Reference panel (FIG. 1, FIG. 6A, FIG. 6C, FIG. 9) base station (FIG. 9). The Base Station includes 1 Soil Monitoring Panel (FIG. 1, FIG. 6A, FIG. 6B, FIG. 9), 1 Reference Panel (FIG. 1, FIG. 6A, FIG. 6C, FIG. 9), and an Automated Cleaning System (FIG. 1, 9, 10, 11, 13). Additional Measurement Units (FIGS. 1, 2A, 2B, 6A), and Comms units (FIG. 1, 7A, 7B) are installed to record the measurements from each soil monitoring panel (FIG. 1, FIG. 6A, FIG. 6C, FIG. 9) and communicate this back to a Base Station (FIG. 9) or master Comms Units (FIG. 1, FIG. 5) where the information is collected and sent to a server (FIG. 1). In this way the soiling measurements at any given location in the PV system can be monitored.

Normalization

Normalization is the process of ensuring that in the clean state, both the soil monitoring panel (FIG. 1, FIG. 6A, FIG. 6B, FIG. 9) and the reference panel (FIG. 1, FIG. 6A, FIG. 6C, FIG. 9) measure precisely the same current. Due to non-uniform rates of degradation and drifting, it is necessary to recalibrate the reference panels (FIG. 1, FIG. 6A, FIG. 6C, FIG. 9) with the Soil Monitoring Panels (FIG. 1, FIG. 6A, FIG. 6C, FIG. 9) on a regular basis. The panels are re-calibrated after each manual cleaning of the native PV system. The normalization button (FIG. 1, FIG. 5) is a moment switch or similar electronic switch that is capable of sending a signal to the Comms Unit (FIG. 1, 7A, 7B) of the Soil Monitoring Panel(s) (FIG. 1, FIG. 6A, FIG. 6B, FIG. 9) when the normalization button (FIG. 1, FIG. 5) is pressed. The normalization button (FIG. 1, FIG. 5) is mounted in an accessible location on the Soil Monitoring Panel (FIG. 1, FIG. 6A, FIG. 6B, FIG. 9) enclosure or panel structure. The button (FIG. 1, FIG. 5) is connected to the Comms Unit (FIG. 1, 7A, 7B) or in another embodiment, the Normalization button (FIG. 1, FIG. 5) is connected to the Measurement Unit (FIGS. 1, 2A, 2B, 6A), The button (FIG. 1, FIG. 5) is pressed when the entire PV system and the Soil Monitoring panels (FIG. 1, FIG. 6A, FIG. 6B, FIG. 9) have been cleaned. Pressing the button (FIG. 1, FIG. 5) indicates that a manual clean has been performed in order to update the web-based tools (Forecast tools) to indicate that a manual clean has been completed. The pressing of the normalization button (FIG. 1, FIG. 5) also starts the process of re-calibrating the soil monitoring panels (FIG. 1, FIG. 6A, FIG. 6B, FIG. 9) with the clean reference panel (FIG. 1, FIG. 6A, FIG. 6C, FIG. 9) thereby ensuring that any changes in the panels (due to drift, or degradation, damage, and or mismatch) of the panel cells is accurately accounted for after each manual cleaning of the native system.

TABLE 2

Figure 3:
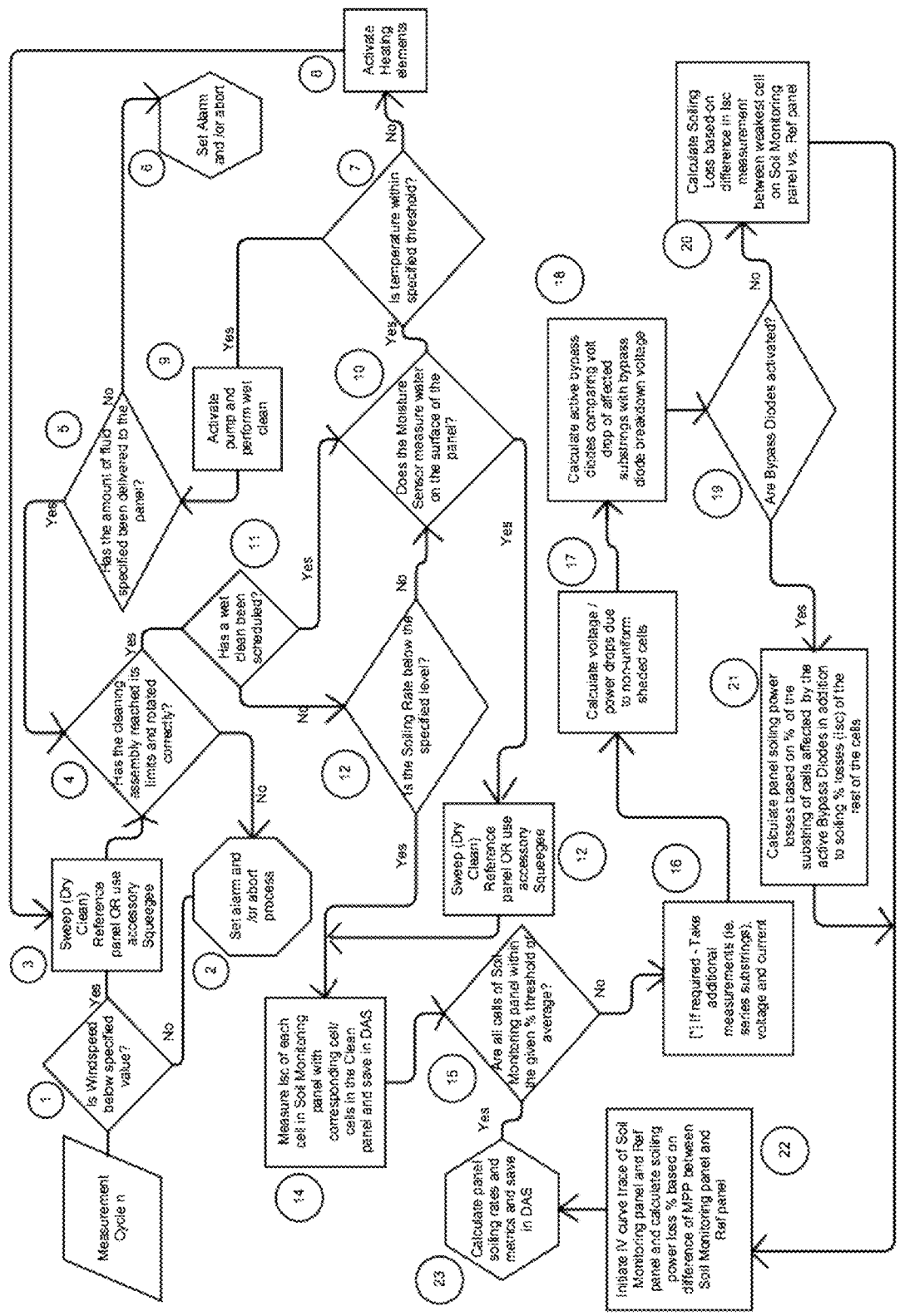
FIG. 3 shows flowchart of measurement cycle processing steps in a solar panel soiling monitoring system according to the present invention.
Figure 4:
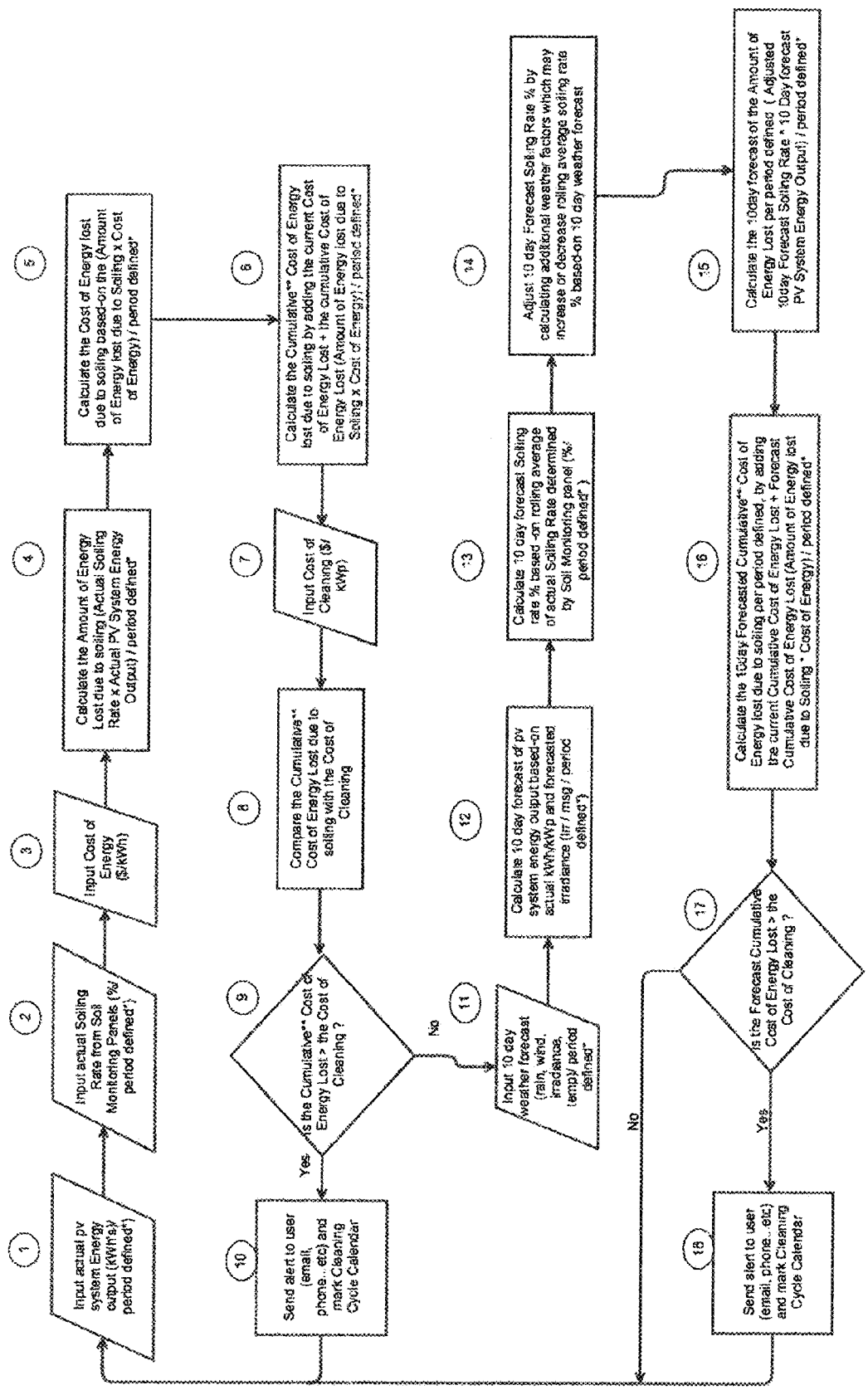
FIG. 4 PV Clean Cycle Forecast Flowchart
Figure 5:
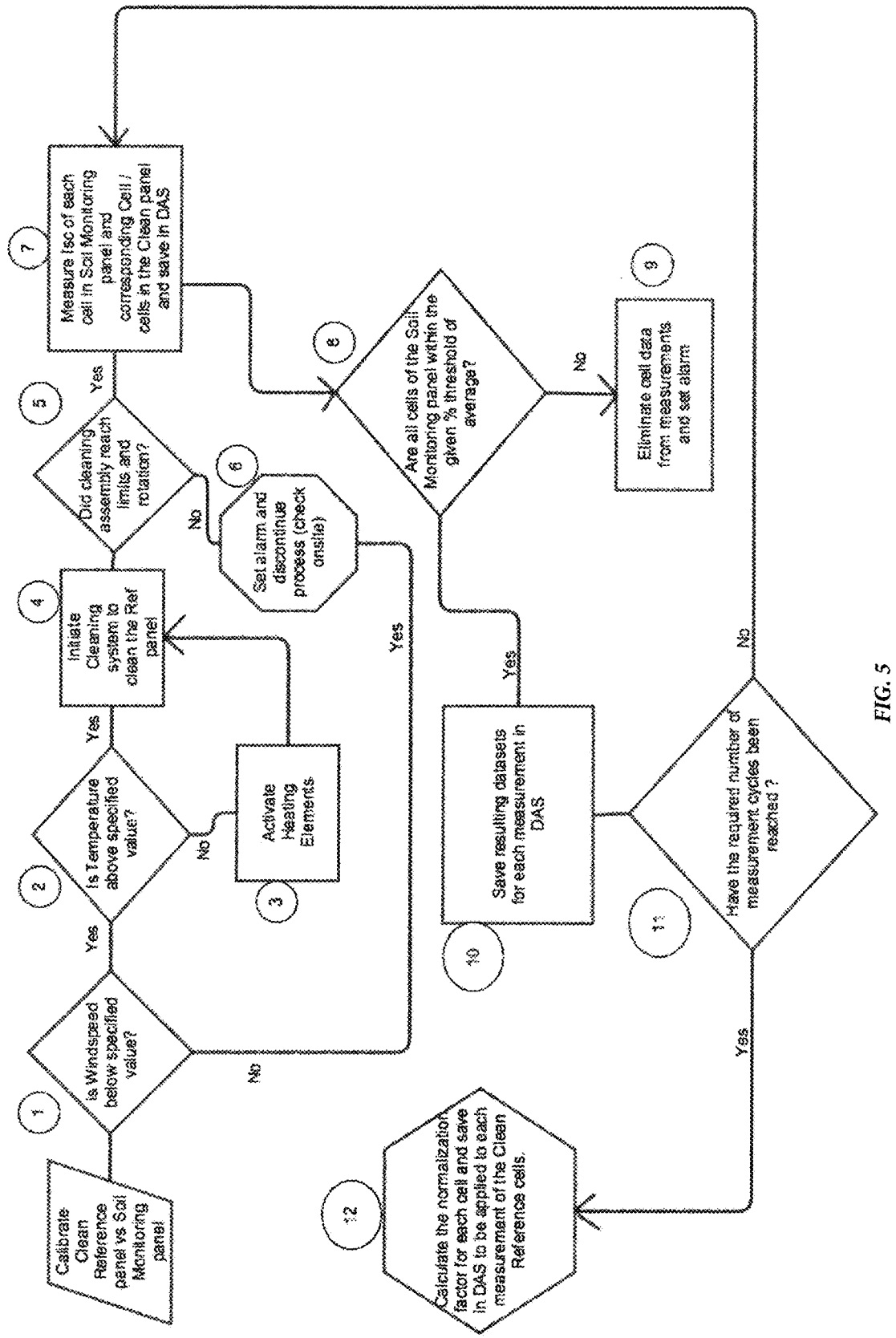
FIG. 5 shows a flowchart of the normalization process in a solar panel soiling monitoring system according to the present invention.

Normalization Processing
By providing a physical button on-site, the normalization process can be coordinated at the precise moment when a manual clean has been performed, thereby ensuring that the soil monitoring panel (FIG. 1, FIG. 6A, FIG. 6B, FIG. 9) maintains an equivalent soiling state as the native PV system.
Normalization processing is shown in FIG. 5 and described in Table 3.
Measurement cycle processing is shown in FIGS. 3 and described in Table 4.

| Step | Task |
|---|---|
| 1 | Is Windspeed below specified value? No: 6 Yes: 2 |
| 2 | Is Temperature above specified value OR heating elements been activated? No: 5 Yes: 4 |
| 3 | Activate heating elements goto 4 |
| 4 | Initiate automated cleaning system to clean reference cell |
| 5 | Did cleaning assembly reach limits and rotation? No: 6 Yes: 7 |

TABLE 2-continued

Normalization Processing
By providing a physical button on-site, the normalization process can be coordinated at the precise moment when a manual clean has been performed, thereby ensuring that the soil monitoring panel (FIG. 1, FIG. 6A, FIG. 6B, FIG. 9) maintains an equivalent soiling state as the native PV system. Normalization processing is shown in FIG. 5 and described in Table 3. Measurement cycle processing is shown in FIGS. 3 and described in Table 4.

| Step | Task |
|---|---|
| 6 | Set alarm and discontinue process |
| 7 | Measure Isc of each cell in Soil Monitoring panel and simultaneously with the corresponding cell in the Clean Reference panel and save in DATA STORAGE SYSTEM |
| 8 | Are all cell measurments of the Soil Monitoring panel within the specified % of average? No: 9, Yes: 10 |
| 9 | Eliminate cell data from measurement datasets and set alarm. |
| 10 | Save resulting measurements for each dataset in the data storage system |
| 11 | Have the specified number of measurement cycles been reached ? No: 7, Yes 11 |
| 12 | Calculate the average normalization factor for each cell on the Soil Monitoring panel as the average difference between Isc measurements between each cell of the Soil Monitoring panel and the corresponding Reference cell and save in DATA STORAGE SYSTEM (FIGS. 1, 2A, 2B, 7A, 7B) to be applied to each measurement of the Clean Reference cells; end |

TABLE 3

Measurement Cycle Processing

| | |
|---|---|
| 1 | Wind-speed below specified value? No: 2, Yes: 3 |
| 2 | Set alarm and/or abort process |
| 3 | Initiate cleaning system |
| 4 | Has cleaning assembly reached its limits and rotated correctly? No: 2, Yes: 11 |
| 5 | Has the cleaning fluid been sensed by the moisture sensor? No: 6, Yes: 4 |
| 6 | Set alarm and/or abort process |
| 7 | Is temperature within specified value: No: 8, Yes: 9 |
| 8 | Activate Heating elements |
| 9 | Activate pump and perform wet cleaning |
| 10 | Does moisture sensor measure water on surface of the ref panel? No: 7, Yes: 13 |
| 11 | Has wet clean been scheduled? No: 12, Yes: 10 |
| 12 | Is the soilng rate determined by the Soil Monitoring panel below the specified level? No: 10, Yes: 14 |
| 13 | Sweep Reference panel with dry brush or dry squeegee |
| 14 | Measure Isc of each cell of Soil Monitoring panel simultaneously with corresponding Clean Reference cell and save results in DAS |
| 15 | Are all cell measurements of Soil Monitoring panel within the specified % threshold of the average? No: 16, Yes: 23 |
| 16 | If required take additional measurements |
| 17 | Calculate voltage loss/power loss as a function of Isc for non-uniform soiling |
| 18 | Calculate forward Bypass diodes comparing voltage drop of affected cells or substrings with breakdown voltage of bypass diodes |
| 19 | Are bypass diodes in forward bias ? No: 20, Yes: 21 |
| 20 | Calculate max soiling loss % based-on weakest cell Isc in Soil Monitoring panel vs. the clean Reference panel. |
| 21 | Calculate Soiling Panel power loss % based-on substrings affected by active bypass diodes by subtracting power contributed by the affected panel substrings from the total panel power. |
| 22 | Initiate IV curve trace of series connected cells of Soil Monitoring panel simultaneously with Ref panel and calculated soiling power loss % based on difference of MPP between Soil Monitoring panel and Reference panel |
| 23 | Calculate panel Soiling rates and metrics and save in Data Storage System |

Bypass Diodes

For embodiments with bypass diodes included in the native photovoltaic panels, the result with bypass diodes can be simulated by calculating the Voltage as a function of Isc and series resistance of each cell in the soil monitoring panel (FIG. 1, FIG. 6A, FIG. 6B, FIG. 9). The differences in cell voltages between surrounding cells of the Soil Monitoring Panel (FIG. 1, FIG. 6A, FIG. 6B, FIG. 9) can be compared with the breakdown voltage of diodes of the native panels to determine when the diodes will be forward biased, thereby eliminating these cells from contributing any power (reducing the power of the panel by subtracting the power of each cell that would be bypassed by the forward bypassed diode in the native panel). The loss of power due to active bypass diodes can be calculated by subtracting the calculated power from each cell(s) of the monitoring panel (FIG. 1, FIG. 6A, FIG. 6B, FIG. 9) affected by active bypass diodes.

Bypass Switch

A Bypass Unit (8A, 8B) provides a means of connecting the PV Soil Monitoring panel (FIG. 1, FIG. 6A, FIG. 6C, FIG. 9) or a standard PV panel, in-series with the rest of the PV panels in a string or array, while isolating this panel to take periodic soil measurements.

The Bypass unit (8A, 8B) can be connected to any number of standard PV panels and/or a Soil Monitoring Panel (FIG. 1, FIG. 6A, FIG. 6C, FIG. 9) as described above. Before taking a comparative measurement (Isc and/or MPPT) the MCU of the Comms unit (FIG. 1, 7A, 7B) will short the incoming series connection around the panel(s) to be measured (8A) In this way the panel(s) to be measured are isolated from the PV system while the Isc/MPPT is measured, and the rest of the panels in the string/array can continue to produce power (less the panel(s) to be measured). After the measurements have been taken, the MCU signals the Bypass Unit (8A, 8B) to re-connect the Soil Monitoring panel(s) (FIG. 1, FIG. 6A, FIG. 6B, FIG. 9) or Standard PV panel(s) to be measured, with the series string of PV panels, so that they can continue to contribute power to the pv array.

Automated Cleaning System

In order to ensure that the reference cell (FIG. 1, FIG. 6A, FIG. 6C, FIG. 9) or panel continues to accurately measure the irradiance, the cell/panel must remain clean and free of debris, in order to ensure reliable and accurate measurements of irradiance.

Most PV reference cells are installed at remote sites where access to the site is not easy or frequent. Cleaning remote equipment by hand is expensive (sending a tech to the remote site) and often not practical to do on a frequent basis.

There is a need for a low cost, reliable, fully automated cleaning system for remotely and effectively cleaning the reference panel, without leaving residues, or having to replenish solvent storage tanks.

In order to establish a reference for the performance of PV systems, a Reference cell or Reference panel is used to calibrate the irradiance to a suitable environmental condition (usually 1000 W/m sq).

In order to ensure that the reference cell or panel continues to accurately measure the irradiance, the cell/panel must remain clean and free of debris, which may interfere with the amount of light reaching the cell, in order to ensure reliable and accurate measurements of irradiance.

Most PV reference cells are installed at remote sites where access to the site is not frequent. Cleaning remote equipment by hand is expensive (sending a tech to the remote site) and often not practical to do on a frequent basis.

Typically automated cleaning systems require water/solvent to clean the surface of the panels. This is problematic in remote desert climates where it is difficult to continually refill the water supply. Water in itself is also not sufficient in itself of completely cleaning the reference panel in all cases. Cleaning with only a wiper and solvent can cause scratches unless a large quantity of solvent is used, requiring a large tank of solvent to clean regularly and effectively. Using a solvent can also cause dust and debris in the air to stick to the wet panel.

There is a need for a low cost, reliable, fully automated cleaning system for remotely and effectively cleaning the reference panel, without leaving residues, or having to continually replace solvent tanks. The invention claimed here solves this problem.

An automated mechanism for cleaning a reference cell/panel is considered, which uses a combination of wet and/or dry cleaning methods to ensure minimum maintenance costs while ensuring that the panel surface is free of dust and residues.

The claimed invention differs from what currently exists. The system is able to clean the panel with and/or without water. The majority of the time the system will simply sweep the panel without the use of water. Sensors help to detect when and if the use of water is required. This allows the panel to be cleaned before each measurement (as often as each hour) ensuring accurate measurements and minimal maintenance.

This invention is an improvement on what currently exists. The system is able to clean the panel with and/or without water. The majority of the time the system will simply sweep the panel without the use of water. Sensors help to detect when the use of water is required. This allows the panel to be cleaned before each measurement (as often as each hour) ensuring accurate measurements and minimal maintenance.

Dust that is allowed to sit on the surface of the glass for more than a day is much more difficult to remove. Additionally, debris from oil based pollution, bird droppings, tree sap, require a scrubbing the panel with a mixture of water and brush.

Cleaning with only a wiper and solvent can cause scratches unless a large quantity of solvent is used. Using a solvent can also cause dust and debris in the air to stick to the panel.

Due to the low energy consumption of the system, it can be powered remotely with a solar panel with a minimal battery. The system cleans regularly using a combination of dry cleaning, using a soft brush to sweep the surface, and wet cleaning, using a squeegee to wipe solvent soaked surface. The system is able to conserve solvent and thus reduce the maintenance required, by sweeping the surface of the panel without the use of water or solvents and in this way the dust and debris does not have time to stick to the panel and is easily removed. Sensors can help to determine when additional water/solvent cleaning is required. In this way the water/solvent is conserved, and more effective cleaning is performed with very little maintenance required.

A combination of wiping to rid the surface of granular debris that can scratch the surface and a solvent that is wiped clear with a squeegee is provided to wipe the water/solvent from the panel. In this way the brush remains dry and does not cause any streaking or residues to be left by the dirty wet brush.

The cleaning system includes:
1. Fluid tank (FIG. 13). The tank may be of any size but typically enough fluid to calculate as necessary to clean the panel for a period of 6 months to a year without refill. The liquid may be water, purified water, a cleaning solution, or a mixture.
2. Water tube for transporting water from the nearby Fluid Tank to the water-fed brush.
3. In one embodiment a Spray nozzle may be mounted on the edge of the panel for spraying water/fluid delivered by the pump/tube assembly onto the panel surface to be cleaned.
4. Brush (FIG. 10A) consisting of a handle which mounts to a motor axel, a suitably stiff bristle.
5. In another embodiment, the brush may be a Water-Fed Brush consisting of a handle which mounts to a motor axel, a valve for the introduction of a water tube, a suitably stiff bristle, water jets or holes where water introduced from the tube can be fed out to the bristles and the surface of the reference panel/cell.
6. Squeegee (FIG. 10A, 10B)—an accessory squeegee is mounted to an additional wiper motor which wipes the surface clean after it has been soaked by the spray nozzle or water-fed brush.

7. Wiper motor(s) (FIG. 10A, 10B) which is generally an electric brush or brushless dc motor controlled to rotate a given radius (typically 90 degrees –120 degrees) and reverse motion.
8. Flow Sensor/Control Valve (FIG. 10A, 10B) which senses the amount of water passing through the tube and controls the amount of water to reach the brush.
9. Moisture sensor (FIG. 9) which senses the presence of water on the surface of the reference panel. The moisture sensor may sense the presence of rain water or dew present on the panel or the presence of water from the brush.
10. A limit switch to indicate that the brush assembly/squeegee assembly has reached the extent of its sweep radius. The system may or may not include a limit switch.
11. A fluid level sensor (FIG. 13) to indicate the amount of cleaning fluid available in the tank.
12. A motor controller, (FIG. 13)) consisting of a microprocessor, and voltage regulators which are capable of controlling the speed and direction of the motors, as well as sensor inputs which are used to control when at what speed the motors should be activated.
13. Wind Sensor (FIG. 1) for measuring wind speed, Temperature Sensor for measuring freezing temperatures, and Relative Humidity Sensor. If the wind speed is above a specified amount, water will not be used to clean the panel in order to avoid dust sticking to the panel while it is wet. The system may or may not include a wind sensor or temp sensor.
14. Soil Loss Sensor (FIG. 1, FIG. 6A, FIG. 6B, FIG. 9) for measuring the amount of soiling on the surface of a PV panel. If it is determined that the amount of soiling is heavy, water (or suitable solvent) may be used to clean the panel in addition to brushing the panel dry.
15. Water Pump (FIG. 13) integrated with the water tank or separate from the water tank, pumps the water from the tank through the tube to the brush and/or nozzle or manifold spray assembly. The water pump is controlled by the Motor Controller.
16. An accessory heating element located around the perimeter of the panel in between the glass and the EVA to melt snow and ice from the surface of the panel.
17. Cleaning Bar (FIG. 13)—A ridged bar or ribbed surface is mounted at the extreme side of the panel, at the edge of the sweep radius of the brush, in order to free the brush hairs from accumulated dust and debris.
18. A motor Enclosure (FIG. 10A, 10B) which protects the motors from dust, rain, sun . . . etc. is installed over the motors and mounts to the structure. The motor enclosure (Drawing) consists of 3 parts: the Top Tray which is installed over the motors, and Battery, and the axles of each motor extend through the enclosure and are sealed around the axles. The Bottom Tray which connects to the inside of the top tray so that water cannot enter the enclosure. The Bottom Tray also has space between the two motors to house the Battery for powering the Cleaning System and Measurement Electronics. The Top Cover, which may connect directly to the structure or to any part of the top tray and covers the squeegee and/or brush tools and the Top Tray. The Top Cover consists of three closed sides and one side open so that the brush and/or squeegee may freely exit from the housing. In another embodiment the Top Cover consists of an automated door which closes the 4 the side, and opens upon the exiting of the squeegee and/or brush.
19. A mounting structure (FIG. 15, 16) consisting of a frame, mounting brackets and mounting posts which mount to an existing panel or structure at the same angle. Supporting structure provides mounting of the PV reference panel or surface to be cleaned, and securing it to the ground or to another structure.
20. Charge circuit (FIG. 7A, 7B) for charging a battery via a solar cell which powers the system.
21. In one embodiment a Spray Manifold system (FIG. 10A, 10B) may be attached to the arm of the Squeegee delivers cleaning solution (water or other) to the surface of the PV Reference Cell as the squeegee moves across the PV Reference Cell. The Spray Manifold consists of a tube with Spray Nozzles mounted directly into the body of the tube. The Spray Manifold is mounted to the Squeegee arm assembly such that the spray nozzles are located on the forward side of the squeegee, pointed directly downward towards the surface to be cleaned.
22. In one embodiment a spring Hinge Squeegee system may be installed to attach the squeegee arm to the squeegee blade (FIG. 10A, 10B)—a spring hinge or separate spring and hinge assembly attached to the squeegee in such a way as to allow the squeegee to rotate at an angle in one or both directions in relation to the surface to be cleaned. In another embodiment, a separate spring and hinge may be installed to the same effect. The hinge is intended to allow the squeegee blade to pivot in one direction against the surface to be cleaned. The spring is applied to the hinge and blade in the opposing direction to keep a light force on the squeegee blade and keep the blade in-place when it is at rest. When the surface to be cleaned is dry the squeegee may have difficulty sliding across the surface to be cleaned, and thus the spring hinge allows the squeegee to apply minimal force at a lower angle to the surface to be cleaned.
23. Battery (FIG. 10A, 10B) which is housed inside the Motor Box and powers the Cleaning system motors and electronics.

The Motor Controller (12) takes input from moisture sensor (9), wind sensors (13), and Relative Humidity sensors (13), Temperature sensors (13), the Soil Monitoring sensor (14), and possibly others, to calculate when and if a cleaning is required.

In one embodiment a dry brush (4) sweeps the surface without water as required. In the case that it is determined (by comparison with the Soiling Loss Sensor (14) or by scheduled cleaning) that the surface should be cleaned with a solvent, the pump, pumps the solvent from the solvent tank (1) through a transportation tube (2), to a spray nozzle (3) mounted at the edge of the surface to be cleaned. In another embodiment, the pump pumps the cleaning solution through the tube into a Spray Manifold (21) which is mounted to the arm of the Squeegee (6). The Spray Manifold (21) delivers the solution to the surface of the PV Reference cell (17) in-front of the squeegee (6) wiper blade as the blade moves across the surface of the PV Reference cell(17). The flow sensor (8) controls the amount of water which is sprayed onto the surface to be cleaned.

After soaking the surface to be cleaned with solvent, a separate wiper motor (7) with mounted squeegee (6), wipes the solvent from the surface to be cleaned 16).

In another embodiment a water-fed brush (5) sweeps the surface to be cleaned without water. In the case that it is determined (by comparison with the Soiling Loss Sensor (14) or by scheduled cleaning) that the surface should be cleaned with a solvent, the pump, pumps the solvent from the solvent tank (1) through a transportation tube (2) to the body of the water-fed brush (5) where the solvent is pumped out of the body of the brush (5), soaking the brush hair and the surface to be cleaned. After soaking the surface to be cleaned with solvent, the water-fed brush scrubs the surface to be cleaned to loosen and/or wash aways surface accumulated dirt and debris. In one embodiment a separate wiper motor (7) with mounted squeegee (6), wipes the surface to be cleaned after the water-fed brush has scrubbed the surface. A flow sensor (8) controls the amount of water which enters the brush and onto the surface of the panel. Any combination of squeegee (6) and/or brush(4) or water-fed brush(5) may be used in any sequence to accomplish the cleaning.

The moisture sensor (9) mounted on the panel surface ensures that the water reaches the panel surface. In the case that moisture (e.g. Rain) is already present on the surface of the panel, water will not be withdrawn from the tank. A limit switch(10) placed at the extent of the brush assembly/squeegee assembly sweep, sends a signal when the brush/squeegee arrives at the extreme end of the radius, in order to confirm that the brush assembly is functioning correctly. In another embodiment the motors are controlled by Hall sensors and/or encoders integrated with the motors or an additional accessory on the motors, which specify the position of the motor in relation to the surface to be cleaned.

A fluid level sensor (11) is placed in the fluid tank (1) to indicate when the fluid is low and needs refilling.

The schedule of cleanings may be configured via a remote web server or via a direct interface with the Motor Controller (12).

The radius of the sweep for the wiper motor (7) is between 90-120 degrees, and can be left handed or right handed depending on the mounting of the motor in relation to the surface to be cleaned. The speed of the sweep and the number of sweeps for each cleaning cycle can be set in the microprocessor of the controller (12) or in the wiper motor (7) directly. The brush (4) (5) and/or squeegee the panel and returns to its docking position at the top of the panel. It is also possible to mount brushes, motors and squeegees in other locations (i.e. at the side or bottom of the surface to be cleaned.

A Motor Enclosure (18) is provided at the docking station of the brush/squeegee in order to ensure that the brush (4)(5)/squeegee (6) are protected from sun and dirt accumulating.

A Motor Enclosure (18) is provided to protect the motors from sun, dust, rain . . . etc. and mount the motors to the structure. In some cases the motors may be suitable for exposure to outdoor elements without requiring a separate cover.

The brush (4) (5) body will be made out of a durable, water resistant, sun resistant material. The brush (4) (5) hair will be made of a durable material suitable for cleaning the surface to be cleaned without scratching the surface.

A ridged or ribbed surface, mounted at the extent of the brush sweep will act to free the brush (4) (5) hairs of any accumulated dust.

The supporting structure (19) provides a way to mount the PV reference panel or appropriate surface.

In one embodiment a dry brush (4) sweeps the surface without water as required, by rotating the brush(4) attached to the wiper motor (7) 90 degrees in the direction of the surface and returning to the top of the surface.

In the case that it is determined (by comparison with the Soiling Loss Sensor (14) or by scheduled cleaning set in the Controller (12)) that the surface should be cleaned with a solvent, the pump (15), pumps the solvent from the solvent tank (1) through a transportation tube (2), to a spray nozzle (3) mounted at the edge of the surface to be cleaned. The flow sensor (8) controls the amount of solvent which is sprayed onto the surface to be cleaned and/or the pump (15) is activated for a specified amount of time.

After soaking the surface to be cleaned with solvent, a separate wiper motor (7) mounted parallel to, or directly opposite to the brush motor on the same side of the surface with mounted squeegee (6, 21), wipes the solvent from the surface to be cleaned, by rotating 90 degrees (7) to sweep-out the same surface to be cleaned, in the same (in the case the motors are mounted parallel to each other) opposite direction of sweep (in the case the motors are mounted opposite to each other).

The sequence of sweeping using both the dry brush (4) and the wiper(6) cleaning the same surface is important in order to maintain the brush in the dry state, while co-locating both the brush (4) and wiper (6, 21) at the top of the panel to avoid shading of the PV reference cell. Keeping the brush dry is important in order to avoid streaking of the surface to be cleaned. When the brush is wet, particularly when it has accumulated dust and dirt, sweeping the brush across the surface requires a lot of solvent to rid both the brush (4) and the surface to be cleaned of all soiled residues.

However, by utilizing both a dry brush (4) and a separate wiper (6, 21) it is possible to avoid streaking altogether:
1. Sweep the surface to be cleaned using the dry brush (4) to 90 degrees. Once the brush (4) has reached the limit switch placed at the perpendicular edge of the surface the brush(4) is held at this position.
2. The pump (15) is then activated spraying solvent through the tube(2) and nozzle(3) or Spray Manifold (21) to the surface to be cleaned(17).
3. The wiper(6) then wipes the solvent and soiling residues from the surface to be cleaned and returns back to the position at the top of the surface to be cleaned by rotating the motor (7) backwards 90 degrees.
4. The dry brush (4) then returns to its position directly in front of the wiper(6) at the top of the surface to be cleaned by rotating the motor(7) backwards 90 degrees.

These steps are a possible sequence amongst any other possible combination of sequences that can accomplish the same ends.

In another embodiment a water-fed brush (5) sweeps the surface to be cleaned without water. In the case that it is determined (by comparison with the Soiling Loss Sensor (14) or by scheduled cleaning) that the surface should be cleaned with a solvent, the pump, pumps the solvent from the solvent tank (1) through a transportation tube (2) to the body of the water-fed brush (5) where the solvent is pumped out of the body of the brush (5), soaking the brush hair and the surface to be cleaned. After soaking the surface to be cleaned with solvent, the water-fed brush scrubs the surface to be cleaned to loosen and/or wash aways surface accumulated dirt and debris. In one embodiment a separate wiper motor (7) with mounted squeegee (6), wipes the surface to be cleaned after the water-fed brush has scrubbed the surface. A flow sensor (8) controls the amount of water which enters the brush and onto the surface of the panel. Any combination of squeegee (6) and/or brush(4) or water-fed brush(5) may be used in any sequence to accomplish the cleaning. The moisture sensor (9) mounted on the panel surface ensures that the water reaches the panel surface and/or the amount of solvent is controlled by the timing the operation of the pump.

In the case that the moisture sensor senses moisture (eg. Rain) is already present on the surface of the panel, water will not be withdrawn from the tank.

A limit switch(10) placed at the extent of the brush assembly/squeegee assembly sweep, sends a signal when the brush/squeegee arrives at the extreme end of the radius, in order to confirm that the brush assembly is functioning correctly. In another embodiment, Hall Sensors or and encoder is used to sense the position of the motors.

A fluid level sensor(11) is placed in the fluid tank(1) to indicate when the fluid is low and needs refilling.

The schedule of cleanings may be configured via a remote web server or via a direct interface with the Motor Controller (12).

The radius of the sweep for the wiper motor(s) (7) is between 90-120 degrees, and can be left handed or right handed depending on the mounting of the motor in relation to the surface (17). The speed of the sweep and the number of sweeps for each cleaning cycle can be set in the microprocessor of the controller (12) or in the wiper motor (7) directly. The brush (4) (5) and/or squeegee (6) returns to its docking position at the top of the panel.

A Motor Enclosure (18) is provided at the docking station of the brush/squeegee in order to ensure that the brush (4) (5)/squeegee (6, 21) are protected from sun and dirt accumulating.

A Motor Enclosure (18) is provided to protect the motors from sun, dust, rain . . . etc and mount the motors to the structure. In some cases the motors may be suitable for exposure to outdoor elements without requiring a separate cover.

The brush (4) (5) body will be made out of a durable, water resistant, sun resistant material. The brush (4) (5) hair will be made of a durable material suitable for cleaning the surface to be cleaned without scratching the surface.

A ridged or ribbed surface (17), mounted at the extent of the brush sweep will act to free the brush (4) (5) hairs of any accumulated dust.

The supporting structure (19) provides a way to mount the PV reference panel or appropriate surface to be cleaned. The structure is supported by a separate base mount or can be attached to another structure.

A Flow Chart will be provided to describe the algorithm for the cleaning system

The cleaning system is assembled from the parts described above.

The wind sensor, temperature sensor, RH sensor may not be necessary. The flow sensor, may not be necessary as the moisture sensor will indicate if water has reached the panel surface. The limit switch may not be necessary as an EMF sensor built into the microprocessor of the controller may adequately detect the motion of the brush. The cleaning bar may be located on either side of the surface to be cleaned or left off of the system completely.

The manner in which solvent is applied to the surface to be cleaned may be changed (ie. water may be poured through a tube from on top of the squeegee or the brush, from any side of the panel, from a tank situated above the surface, through a valve, a wetted sponge attached to the squeegee, from a sprayer or tube attached to the top or side of the brush or squeegee).

Alternatively a rotary brush may be used to eliminate dusts and scrub the panel (instead of a wiper). Any combination of squeegee (6, 21) and/or brush(4) or water-fed brush(5) may be used in any sequence to accomplish the cleaning.

The water/solvent may be sprayed onto the panel separate/external to the brush. The brush motor and or squeegee motor may be of any suitable size or type and located on any side of the panel.

The size, and shape of the solvent tank may be any that are suitable or obvious to those in the trade. The size or type of solvent pump may be of any size or type obvious to those in the trade. The surface to be cleaned may be of any size or type.

The automated cleaning system is used to keep the PV reference cell clean and thus ensure the accuracy of the reference measurements.

The system can be used to clean any surface that requires automated cleaning.

The user would install the automated cleaning system on a remote site to ensure that the PV reference panel is always free of debris that may cause inaccurate irradiance measurements.

Additionally: the invention might be used in any field where a surface is required to be cleaned regularly and automatically and/or remotely.

Flexible PV Panel PCB

The Flex PCB (FIG. 6B) provides an easy way to manufacture the PV Monitoring Panels (FIG. 1, FIG. 6A, FIG. 6B, FIG. 9) and Reference Panels described in the previous disclosures. During the construction of the PV Monitoring Panels (FIG. 1, FIG. 6A, FIG. 6B, FIG. 9), the Flex PCB is laid on top of the series connected PV cells and soldered to each of the cell busbars. The insulation on the Flex PCB ensures that the leads from each pv Cell are routed to the respective pins on a connector installed on the Flex PCB (FIG. 6B) which correspond to the respective Measurement Unit (FIGS. 1, 2A, 2B, 6A), connectors without shorting other portions of the PV panel or cells. The Flex PCB (FIG. 6B) ensures that each cell is connected to the connector pins in a precise and secure way.

One set of connectors (plugs) are soldered directly to the Flex PCB (FIG. 6B) which is connected to the PV Monitoring Panels (FIG. 1, FIG. 6A, FIG. 6B, FIG. 9). A connector sized piece of ridged PCB is soldered onto the back of the connector Plugs after the Flex PCB, to give support and rigidity to the Flex PCB portion of the connection.

The FIG. 6B shows a Flex PCB wiring circuit for a 60 cell pv panel, however any number of cells may be connected to any number of connectors in this same way.

Pv Monitoring Panel J-Box and Pv Reference Cell J-Box (Same Design for Both Only Different Form Factors/Sizes)

The J-box (FIG. 2C) seals and secures the connection between the Electronic Measurement Unit (FIGS. 1, 2A, 2B, 6A), Enclosures and the PV Monitoring Panel (FIG. 1, FIG. 6A, FIG. 6B, FIG. 9) and or Reference Panel. There are two parts to the J-box (FIG. 2C) which are connected together upon connecting the Electronics Enclosures (Measurement Unit (FIGS. 1, 2A, 2B, 6A), with the PV Monitoring Panel (FIG. 1, FIG. 6A, FIG. 6B, FIG. 9) or Reference Panel. One part of the J-box is mounted using silicone or similar adhesive, directly on the back of the PV Monitoring panel (FIG. 1, FIG. 6A, FIG. 6B, FIG. 9) or Reference Panel over the top of the Connector Plugs which are exposed to allow direct connection with the counterpart Connector Headers installed on the electronic Enclosures. The other half of the J-box is mounted to the bottom of the electronic enclosures over the top of the Connector plugs.

The Plug connectors are lifted off of the surface of the PV Monitoring Panel approximately 10 mm and fed through a small hole in the J-box (FIG. 2C) where they are mounted on a connector sized mounting ledge provided by the J-box (FIG. 2C) (3 mm off the surface of the PV Monitoring panel). The Connector Capture Cap is then fitted over the top of the connector and holds down the bottom of the connector supported by the J-box ledge, so that it cannot move from its position. This protects the PV cells below the connectors from being damaged during installation, captures the connectors so that they can be plugged and unplugged by removing the enclosures, and aligns the connectors in position.

The connector Headers are mounted on the bottom of the PCB enclosures. The J-box (FIG. 2C) part corresponding to the Enclosures is mounted over the top of the connector and glued (with silicon or other variant) to the bottom of the enclosure, so that the top of the connector Headers are exposed to connect with the Connector Plugs on the PV panel.

A rubber or other type of seal is placed around the perimeter of the J-box (FIG. 2C) on one or both halfs of the J-box (FIG. 2C) to keep out moisture and dust when the two halves of the J-box (FIG. 2C) are mounted together.

In one embodiment screws can be accessed from inside the Enclosure and inserted through the provided holes to secure the two halves of the J-box (FIG. 2C) together. In another embodiment, the body of the J-box (FIG. 2C) includes a latching mechanism which latches the two halves of the J-box together upon pressing the two halves of the J-box into place. A special tool may be used to unlatch the latching mechanism to remove the two halves of the J-box.

Figure 2C:
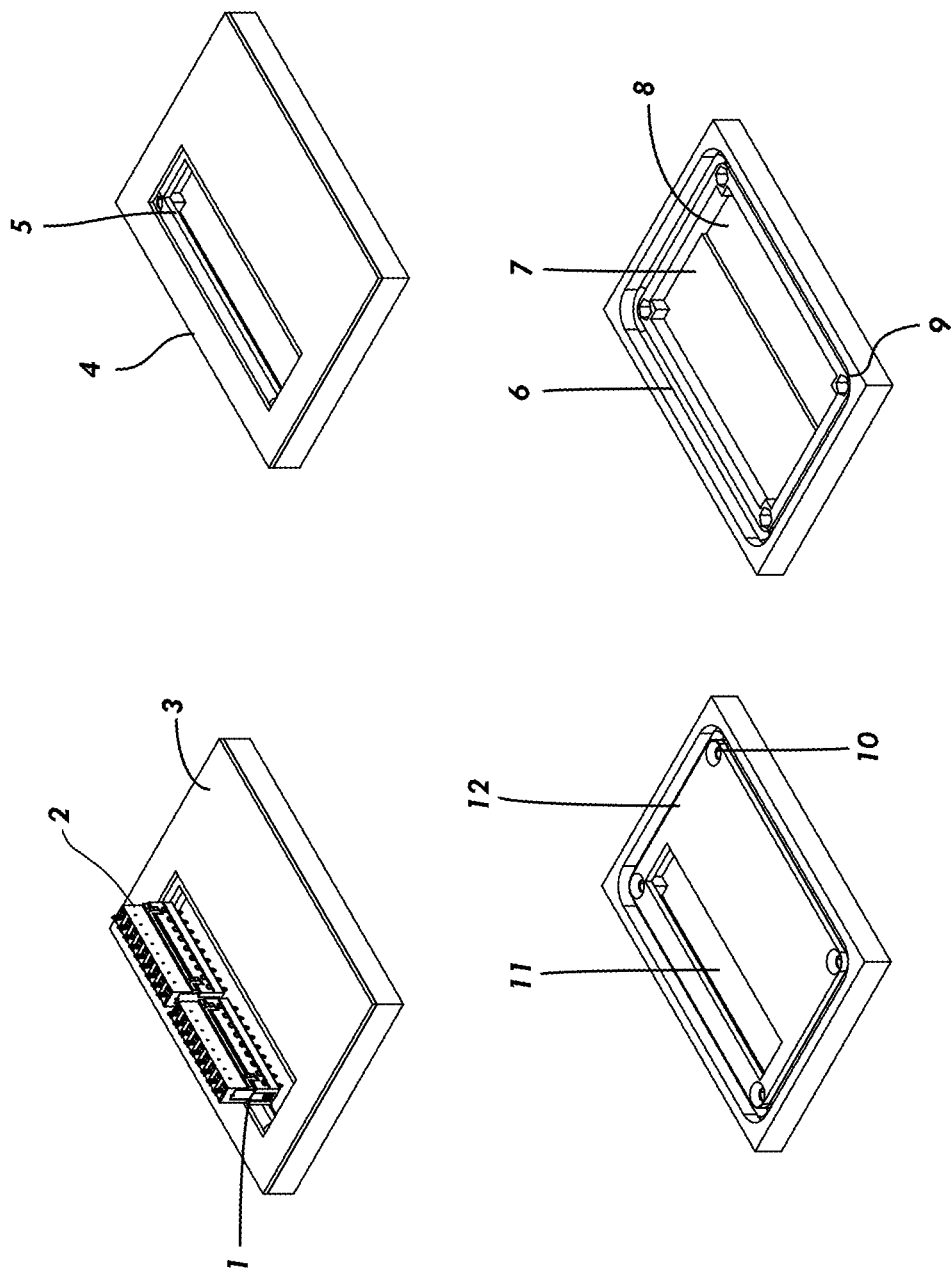
FIG. 2C shows a design for a Junction box that is installed between the Soil Monitoring Panel and/or Reference Panel and the Measurement Units. The Junction box seals the connectors connecting the Soil Monitoring Panel and Reference Panel to the Measurement Unit.

FIG. 2C shows a specific number and configuration of connectors however any number and configuration of connectors may be accommodated by the J-box in this way.

Mounting Structures

Adjustable Bases (FIG. 16) (the bases are detailed in the Automated Cleaning System disclosure). Slight modification to these bases includes additional angular supports to increase the stability of the base and longer slotted leg supports which provide a means for adjusting the height on the back legs. Slotted holes on both sides of the leg supports to provide additional strength.

Framing System

Edge Soiling occurs when dirt pollen and mold accumulate at the border of the frame. The distance from the edge of the cell to the frame is not standard. Furthermore most PV panel frames are fixed to the PV panel making it difficult if not impossible to remove or change frames. The Soil Monitoring Panels (FIG. 1, FIG. 6A, FIG. 6B, FIG. 9) have adjustable frames (FIG. 17) which can be sized according to any standard PV frame in order to best match the boarder distance between cell and frame and exactly simulate the edge soiling effect of any standard PV panel.

The framing system includes an Under Supporting Structure (USS) that matches the same size of the PV panel glass. The top perimeter of the PV Monitoring Panel glass is surrounded with a thin strip of protective material (rubber, silicone, neoprene . . . etc). A standard PV frame of any width is connected by bolts to the USS and clamps to the upper perimeter of the PV Monitoring Panel glass over the protective material, such that it holds the PV Monitoring Panel Glass to the USS.

In the case that a different frame should be requested the frame can be easily removed by removing the bolts to the under supporting frame and and the Panel frame can replaced with a frame of any width.

MPP Module

The details of the MPP Module (FIG. 2A, 2B) are shown in Figure FIG. 2A and FIG. 2B. This includes a pulse width modulated (PWM) current which is swept across the range of values from open circuit to short circuit using a fixed load resistor to gather the measurement of the Panel IV curve. Modulating the power of the PV panel using a PWM signal in conjunction with a Load resistor, a very fast and precise IV curve of the PV panel simultaneously with the IV curve of the PV Reference Cell. The max of each curve is defined to calculate the MPP.

Standard PV Panel

The system can be used with a Standard PV panel. In this case a PWM is used to vary the current through a load resistor and the resulting IV curve is traced for the PV panel simultaneously with the PWM IV curve of the PV Reference Cell. The two Max Power Points are calculated, the difference of the two MPP's is calculated and the % of power lost due to Soiling can be calculated for the portion of the PV system relating to the Soiled PV Panel.

The foregoing description of preferred embodiments of the present disclosure has been presented for purposes of illustration and description. The described preferred embodiments are not intended to be exhaustive or to limit the scope of the disclosure to the precise form(s) disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the concepts revealed in the disclosure in various embodiments and with various modifications as are suited to the particular use contemplated. All such modifications and variations are within the scope of the disclosure as determined by the appended claims when interpreted in accordance with the breadth to which they are fairly, legally, and equitably entitled.

What is claimed is:

1. A solar panel soiling monitoring system for a photovoltaic (PV) system, the monitoring system comprising:
   a soil monitoring panel including a plurality of arranged photovoltaic cells arranged on a rectangular frame and connected in series to one another;
   a measurement unit including a circuit board in electronic communication with a switchbox for controlling measurements of each of the plurality of photovoltaic cells of the soil monitoring panel, the measurement unit in electronic communication with each of the plurality of photovoltaic cells of the solar monitoring panel;
   a communication unit in electronic communication with the measurement unit and including a device for transmitting a detected short circuit current of each individual photovoltaic cell of the plurality of photovoltaic cells; and
   a data storage system in electronic communication with the communication unit including a processor, a computer readable storage medium, and one or more computer programs operable on the data storage system;
   wherein the data storage system determines soiling conditions of the soil monitoring panel based on the detected short circuit currents of each of the plurality of photovoltaic cells of the soil monitoring panel.

2. The solar panel soiling monitoring system of claim 1 further comprising a reference solar panel including at least one photovoltaic cell in electronic communication with the data storage system, wherein the data storage system receives a short circuit current of the at least one photovoltaic cell of the reference solar panel and wherein the data storage system further determines conditions of the soil monitoring panel based on compared measured short circuit currents of each of the plurality of photovoltaic cells of the soil monitoring panel and the at least one photovoltaic cell of the reference solar panel.

3. The solar panel monitoring system of claim 2 further comprising a normalization input in communication with one of the data storage system, the measurement unit, or the communication unit, wherein when an input is detected on the normalization input the data storage system calibrates a detected short circuit current detected from each photovoltaic cell of the soil monitoring panel and the reference solar panel such that any difference between the detected short circuit currents is normalized.

4. The solar panel monitoring system of claim 2, wherein the reference solar panel is positioned at a same azimuth and elevation angle as the soil monitoring panel.

5. The solar panel monitoring system of claim 1, wherein the soil monitoring panel is positioned at a same azimuth and elevation angle as an adjacent photovoltaic system.

6. The solar panel monitoring system of claim 2 wherein the reference solar panel further comprises an automatic cleaning system, the cleaning system including one or more movable cleaning components mounted adjacent to the reference solar panel, the one or more movable cleaning components including one or more motors in communication with a controller, wherein the controller activates the one or more movable cleaning components for cleaning a surface of the reference solar panel.

7. The solar panel monitoring system of claim 6, wherein one of the movable cleaning components comprises a dry brush for sweeping a surface of the reference solar panel.

8. The solar panel monitoring system of claim 6 further comprising a fluid tank and a spray manifold adjacent the reference panel in fluid communication with the fluid tank, wherein one of the movable cleaning components comprises a squeegee.

9. The solar panel monitoring system of claim 8, wherein the spray manifold is mounted to an arm attaching the squeegee to the motor.

10. The solar panel monitoring system of claim 6, further comprising a housing positioned adjacent the reference solar panel for housing the one or more movable cleaning components when not in use.

11. The solar panel monitoring system of claim 1, further comprising one or more environmental condition sensors in electronic communication with one of the data storage system, the communications unit, or the measurement unit, wherein the one or more environmental condition sensors are selected from the group consisting of a temperature sensor, rain or moisture sensor, and a wind sensor.

12. The solar panel monitoring system of claim 1, wherein the soil monitoring panel has a size and dimensions that are proportional to one or more solar panels of an adjacent photovoltaic system.

13. The solar panel monitoring system of claim 1, further comprising a communications module in electronic communication with the measurement unit, wherein the data storage system is located remotely from the soil monitoring solar panel and receives data remotely via the communications module.

14. The solar panel monitoring system of claim 1, further comprising a Bypass Unit, consisting of one or more load break disconnect switches which are controlled by a logic circuit in order to connect and disconnect a plurality of series connected pv panels from a load and connecting or disconnecting the plurality of series connected pv panels from one or more Soil Monitoring panels.

15. The Bypass Unit of claim 14 further comprising switching devices in communication with one of the logic circuit, and the communications unit, the switching devices for controlling the connection or disconnection of one or more Soil Monitoring panels to the Measurement Unit.

16. The solar panel monitoring system of claim 1, further comprising a bypass switch in electronic communication with the plurality of photovoltaic cells connected in series and in communication with the communication unit, wherein when the bypass switch is activated the plurality of series connected photovoltaic cells are disconnected from a power supply and from the soil monitoring panel to be measured for soiling loss, and reconnected to the power supply albeit without connection to the soil monitoring panel to be measured for soiling loss; wherein when the soiling loss measurements have been taken, the communication unit signals for the Bypass Switch to disconnect the plurality of series connected photovoltaic cells from the power supply once again, and reconnect the soil Monitoring panel to the plurality of series connected photovoltaic cells and to the power supply.

17. The solar panel monitoring system of claim 1, further comprising a forecasting module implemented on the data storage system or a remote server, wherein the forecasting module determines a future cleaning schedule of a photovoltaic system based-on the determined soiling rate of the soil monitoring panel.

18. A method of determining a soiling condition of a photo-voltaic system, the method comprising:
providing a soil monitoring panel having a plurality of arranged photovoltaic cells;
providing a measurement unit in electronic communication with each of the individual photovoltaic cells of the soil monitoring panel;
providing a data storage system including a processor, a computer readable storage medium, and one or more computer programs operable on the data storage system;
providing a communications unit for communicating with a server database;
measuring a short circuit current of each of the individual photovoltaic cells via a switchbox on the measurement unit;
comparing the measured short circuit current of each of the individual photovoltaic cells of the soil monitoring panel with each other;
determining soiling conditions of the soil monitoring panel based on measured and compared short circuit currents of the individual photovoltaic cells.

19. The method of claim 18, further comprising:
providing a reference solar panel including at least one reference photovoltaic cell;
measuring a short circuit current of the at least one reference photovoltaic cell on the data storage system;
measuring a maximum power point of at least one reference photovoltaic cell connected to the measurement unit;
comparing measured short circuit currents of the individual photovoltaic cells with each other;
determining soiling conditions of the soil monitoring panel based on measured and compared short circuit currents of the individual photovoltaic cells and the reference photovoltaic cell.

20. A solar panel soiling monitoring system for a photovoltaic (PV) system, the monitoring system comprising:
a soil monitoring panel including a plurality of arranged photovoltaic cells;

a measurement unit including a circuit board in electronic communication with each of the plurality of photovoltaic cells of the soil monitoring panel;

a communications unit for receiving a short circuit current from each individual photovoltaic cell of the plurality of photovoltaic cells via a junction box; and a data storage system including a processor, a computer readable storage medium, and one or more computer programs operable on the data storage system;

a reference solar panel including at least one photovoltaic cell in electronic communication with the data storage system, wherein the data storage system receives a short circuit current of the at least one photovoltaic cell of the reference solar panel and wherein the data storage system further determines conditions of the soil monitoring panel by comparing measured short circuit currents of each of the plurality of photovoltaic cells of the soil monitoring panel with the at least one photovoltaic cell of the reference solar panel; and wherein the data storage system determines conditions of the soil monitoring panel based on compared measured short circuit currents of each of the plurality of photovoltaic cells of the soil monitoring panel and the at least one photovoltaic cell of the reference solar panel.

* * * * *